US005245665A

United States Patent [19]

Lewis et al.

[11] Patent Number: 5,245,665

[45] Date of Patent: Sep. 14, 1993

[54] METHOD AND APPARATUS FOR ADAPTIVE AUDIO RESONANT FREQUENCY FILTERING

[75] Inventors: Michael P. Lewis; Timothy J. Tucker; Doran M. Oster, all of Gainesville, Fla.

[73] Assignee: Sabine Musical Manufacturing Company, Inc., Gainesville, Fla.

[21] Appl. No.: 713,983

[22] Filed: Jun. 12, 1991

Related U.S. Application Data

[63] Continuation-in-part of Ser. No. 537,774, Jun. 13, 1990.

[51] Int. Cl.[5] .......................... A61F 11/06; H04B 15/00

[52] U.S. Cl. .......................................... 381/71; 381/93

[58] Field of Search ........................ 381/71, 83, 93, 94, 381/66, 95, 96, 103, 104, 108, 72

[56] References Cited

U.S. PATENT DOCUMENTS 4,079,199 3/1977 Patronis, Jr. .
4,091,236 7/1978 Chen .
4,165,445 7/1979 Brosow .
4,232,192 11/1980 Beex ........................ 381/83
4,238,746 12/1980 McCool et al. ................ 333/166
4,382,398 6/1983 O'Neill .
4,449,237 3/1984 Stepp et al. .
4,493,101 11/1985 Muraoka et al. .
4,602,337 4/1986 Cox .
4,620,069 6/1986 Godwin et al. .
4,630,304 12/1986 Borth et al. ................ 381/71
4,649,505 3/1987 Zinser et al. ................ 381/94
4,658,426 4/1987 Chabries et al. ............. 381/93
4,817,160 7/1989 De Koning et al. .
5,027,410 6/1991 Williamson et al. ........... 381/68.4
5,029,217 7/1991 Chabries et al. ............. 381/68.2
5,046,101 9/1991 Lovejoy ..................... 381/72

*Primary Examiner*—James L. Dwyer
*Assistant Examiner*—Jack Chiang
*Attorney, Agent, or Firm*—Donald W. Marks

[57] ABSTRACT

Audio signals are digitized and an FFT is conducted on samples of the digitized signals to produce corresponding frequency spectrums. These spectrums are analyzed, such as by determining one or more peak frequency magnitudes which are 33 dB greater than harmonics or subharmonics of the frequency in a plurality of several successive spectrums, to detect resonating feedback frequencies. The offending frequency is then filtered in the time domain, either in the digitized form or analog form, to eliminate the feedback.

53 Claims, 15 Drawing Sheets

METHOD AND APPARATUS FOR ADAPTIVE AUDIO RESONANT FREQUENCY FILTERING

CROSS-REFERENCE TO RELATED APPLICATION

This application is a continuation-in-part application of U.S. application Ser. No. 07/537,774 filed Jun. 13, 1990, by Michael P. Lewis for MICROPROCESSOR CONTROLLED FEEDBACK EXTERMINATOR AND METHOD FOR SUPPRESSING ACOUSTICAL FEEDBACK, which application in its entirety is hereby incorporated herein by reference.

TECHNICAL FIELD

The present invention relates generally to a device and method for suppression of feedback in electrical amplification systems and more particularly to adaptive filtering of resonating feedback frequencies from electrical signals generated by a microphone and used in the generation of amplified signals to drive one or more speakers in the vicinity of the microphone.

BACKGROUND ART

In electrical audio amplification systems, resonant acoustical feedback results from the transmission and/or reflection of sound waves between a speaker and a microphone and the in-phase amplification of the electrical sound signals between the microphone and the speaker. Acoustic resonant properties vary greatly at different frequencies with different transmission, reflection and absorption properties of different rooms and with different positioning of microphones, speakers and other objects in rooms. When amplification or volume is set to a desired level, there often occurs acoustic resonant feedback at one or more frequencies. Acoustical resonant feedback, if not filtered to eliminate the resonant feedback, overwhelms the desired audio signal to produce an extremely loud, unpleasant tone.

A notch filter, or a band reject filter, is a well known device for attenuating electrical signals between any two specified frequencies while not appreciably affecting signals at other frequencies outside this band or channel. A notch filter tuned to a center frequency equal to a feedback frequency may be utilized for suppression of the feedback by holding the amplitude of the feedback signal below unity gain. However because the frequency of acoustical feedback is unpredictable and may occur at almost any frequency within the audio frequency spectrum extending from approximately 20 to 20,000 Hz, the frequency of the notch filter or filters in sound amplification systems must be individually selected for the particular rooms or locations of the microphones and speakers of the sound amplification systems. Also the required attenuation varies with different locations.

Graphic or parametric equalizers are often used in the electrical amplification circuit to suppress acoustical feedback. These equalizers employ a plurality of adjustable attenuators with respective bandpass filters, or adjustable notch filters, tuned to successive frequency bands or channels spanning the audio frequency range. By increasing the attenuation of the frequency band or bands containing the undesirable resonant feedback frequency or frequencies to reduce amplification the acoustical feedback can be eliminated.

In practical applications the operator of a graphic equalizer tries to equalize the sound system before the performance. After the speakers, microphones and amplifiers have been installed, the operator turns the volume of the amplifier up until feedback occurs. The operator then adjusts the controls that control the attenuation of the notch filters until the feedback is eliminated. Often several tries are required to get the right setting. It is not uncommon for more than one filter to be required for a single resonance if the resonance occurs between two adjacent bands. Next, the operator increases the volume of the amplifier until the next resonance occurs and repeats the process. This process is usually repeated until three or four resonant frequencies are attenuated.

Once the program begins, the operator must be vigilant in case new resonant frequencies occur during the program. This is common because microphones frequently are moved during a performance and a room full of people often has different acoustic characteristics than when it is empty.

In many cases, churches, schools, clubs, and small bands that use sound amplification equipment do not have trained sound system operators. The amplification system is often installed by a professional who adjusts the graphic equalizer for an empty room. Oftentimes, the unattended system resonates during a program, and an untrained user changes the equalizer until the resonance disappears. Changing the equalizer can result in excessive distortion of the music or the voice of the speaker using the microphone. The next day, a professional is called who equalizes again for an empty room. Thus, there is a continuing problem.

Graphic equalizers have limitations in the number and the bandwidth of the channels which they control. In expensive professional systems, the equalizer can have sixty-two channels wherein each channel covers one-sixth of an octave. Substantial attenuation of three or four channels can introduce substantial distortion of the sound spectrum. Such distortion is even more likely with less expensive systems employing fewer channels of greater bandwidth.

Adaptive suppression of acoustic resonant feedback is taught in the prior art as exemplified in U.S. Pat. No. 4,079,199 to Patronic, Jr., U.S. Pat. No. 4,091,236 to Chen, U.S. Pat. No. 4,165,445 to Brosow, U.S. Pat. No. 4,382,398 to O'Neill, U.S. Pat. No. 4,493,101 to Muraoka et al., U.S. Pat. No. 4,602,337 to Cox, U.S. Pat. No. 4,658,426 to Chabries et al., and U.S. Pat. No. 4,817,160 to De Koning et al. The adaptive systems include facilities for detecting the presence of resonant feedback and its frequency or the channel in which its frequency is found. Filtering is then performed in response to the resonant frequency detection. Several systems divide the electrical signal from the microphone into several channels spanning the audio spectrum and then lower the amplification or increase the attenuation of the channel or channels containing the resonant frequency or frequencies. Some systems utilize one or more frequency adjustable notch filters, such as switched capacitance filters, which are tuned to the resonant frequency or frequencies in response to the resonant frequency detection.

While the prior art adaptive systems provide automated alternatives to manually operated graphic equalizers, there still exists a need for automated acoustic feedback suppression with minimum sound distortion at a reasonable cost. The prior art adaptive systems generally have one or more deficiencies such as tending to produce excessive sound distortion, being excessively expensive, being excessively large, etc.

SUMMARY OF INVENTION

The present invention is summarized in a method and apparatus for eliminating acoustical feedback in a sound amplification system wherein electrical signals from a microphone are digitized by an analog-to-digital convertor for periodically producing a predetermined series of digital signals which are then converted to a frequency spectrum by a Fast Fourier Transform in a computer. Successive frequency spectrums are examined by the computer to determine the presence of an acoustic resonating feedback signal, and one or more filter devices are controlled by filter control signals from the computer for attenuating one or more narrow frequency bands in the electrical signal to eliminate undesirable acoustic feedback.

In a further feature of the invention, each frequency spectrum is examined to determine a maximum magnitude frequency which is then compared with the magnitude of one or more harmonics and/or subharmonics of the maximum magnitude frequency to determine if the maximum magnitude frequency is greater by at least a predetermined factor to indicate a candidate resonating feedback frequency. The presence of a candidate resonant frequency in a plurality of a predetermined number of successive spectrums indicate the candidate resonant frequency is a resonating frequency to be attenuated.

In one embodiment, filtering is accomplished by using a second computer such as a microprocessor with a digital filter algorithm to digitally attenuate one or more narrow frequency bands from the electrical signal.

In a second embodiment, the computer operates programmable notch filters such as switched capacitor filters to suppress audio feedback resonance.

It is, therefore, an object of the invention to provide an apparatus and method for quickly, accurately and precisely determining the presence of acoustical resonating feedback in an audio signal and thereupon suppressing the feedback by utilizing a computer such as a microprocessor to periodically monitor time segments of the signal and control a filter device or devices.

Another object of the invention is to accurately control the frequency, bandwidth and attenuation of filter devices to selectively attenuate one or more narrow frequency bands of the signal without affecting other desired portions of the audio signal.

One advantage of the invention is that the number of components is kept to a minimum to suppress feedback resonance with minimum sound distortion and minimum cost.

Another advantage of the invention is the recognition that acoustic resonating feedback signals are generally not accompanied by harmonics whereas desirable voice and music tones are generally rich in harmonics.

Additional features of the invention include the provision of an increased number of filters to increase the ability to filter feedback; the decrease in the width of the feedback filters to decrease tonal degradation; the increase in the frequency adjustment range of the feedback filters to enable filtering of substantially any frequency in the audio spectrum; the provision of low and high end roll-off filters (shelving filters) to improve the ability to control the sound; the elimination of the need for threshold adjustment to make operation even simpler; the increase in the dynamic range, signal to noise ratio, filter placement resolution, filter depth control, and spectral variation; the provision of facilities for initially determining where feedback is likely to occur with the automatic initial setup of filters; the reduction in the size of the printed circuit board allowing installation in public address systems and mixers; and the provision of a keyboard and display to enable user selection of the number of fixed, floating and inactive filters with display of the frequency response curve provided by the low and high end rolloff filters as well as the frequencies and depths of the feedback filters.

Other objects, advantages and features of the invention will be apparent from the following description of the preferred embodiment taken in conjunction with the accompanying drawings wherein:

DESCRIPTION OF THE PREFERRED EMBODIMENTS

Figure 1:
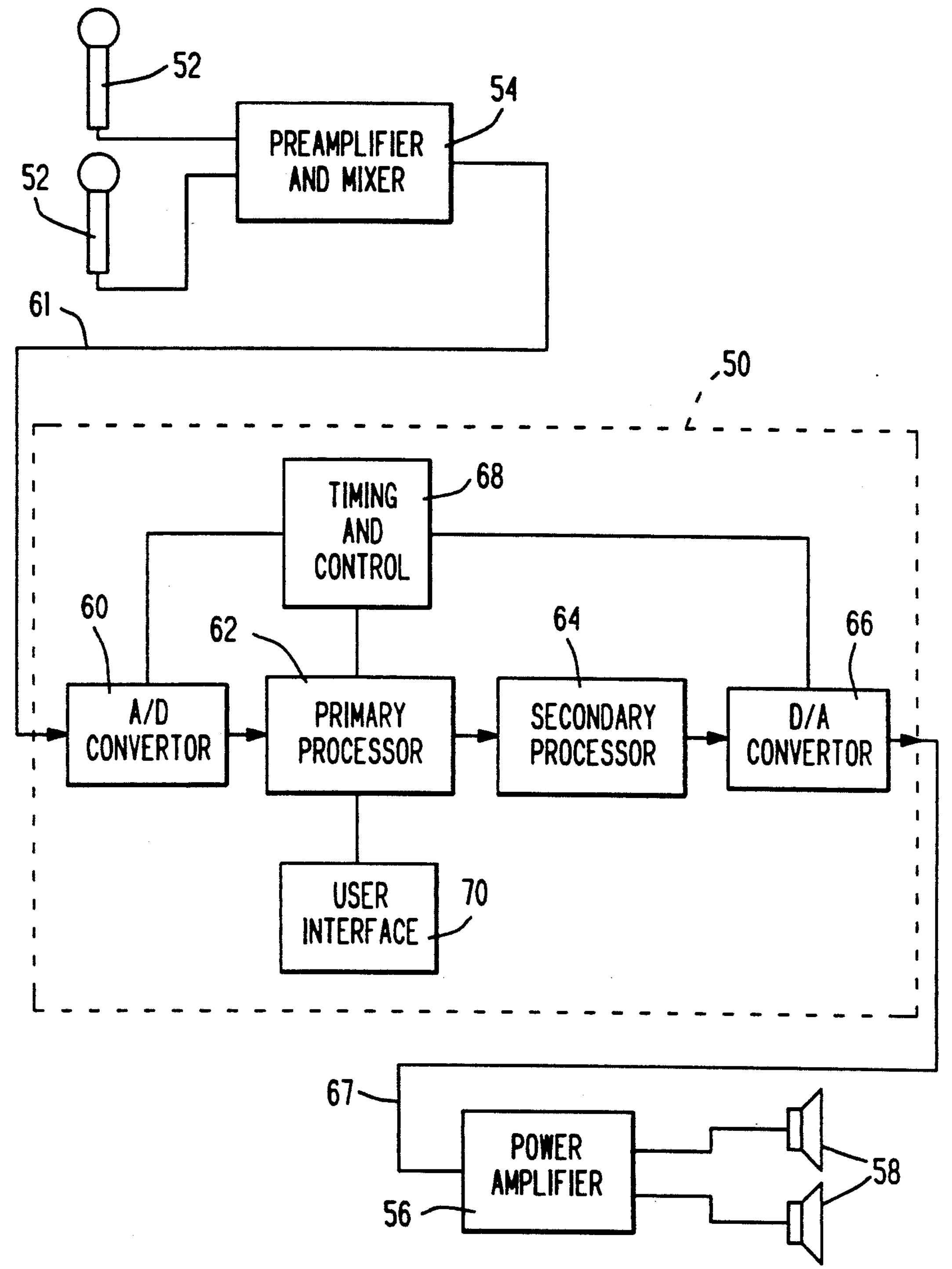
FIG. 1 is a block diagram of a sound amplifier system with an adaptive resonant feedback filtering circuit in accordance with the invention.

As shown in FIG. 1, one embodiment of an electrical sound amplification system in accordance with the invention includes a circuit indicated generally at 50 for adaptively filtering resonant frequencies from the electrical signals. A typical sound amplification system includes one or more microphones 52 which convert sound into electrical signals applied to a preamplifier and mixing circuit 54. The adaptive filtering circuit 50 is interposed between the preamplifier circuit 54 and a power amplifier circuit 56 which drives one or more speakers 58 which are in the same room or vicinity of the microphone 52. Resonating feedback frequencies are detected by the adaptive filtering circuit 50 which attenuates the feedback frequencies to levels where they can not be picked up and progressively amplified from the sound generated by the speaker.

The adaptive resonant frequency filtering circuit 50 of FIG. 1 includes an analog-to-digital convertor 60 which converts the analog signal from the microphone 50 on line 61 to a continuous series of digital signals. These digital signals are passed to a primary computer or processor 62 which in turn passes the digital signals to a secondary computer or processor 64. The primary processor 62 periodically collects a series of the passing digital signals and conducts a Fast Fourier Transform (FFT) on each collected series of the digital signals. Frequency spectrums produced by the FFT are examined by the primary processor to discover the presence of any resonating feedback frequency. Filter control signals are passed by the primary processor 62 along with the digital sound signals to the secondary processor 64 which operates a digital filtering algorithm in accordance with the filter control signals to attenuate resonating feedback frequencies in the stream of digital signals. These digitally filtered signals are then passed by the secondary processor to a digital-to-analog convertor 66 which converts the stream of digital signals back into an analog signal outputted over line 67 to the power amplifier 56. Timing and control circuit 68 generates the timing signals necessary to properly pass the digital stream through the unit 50. User interface 70 is used to connect the unit to a keyboard and display device so that various parameters can be displayed and adjusted by an operator.

The analog signals 61 and 67 together with the digitized stream of signals passed through the primary processor 62 and the secondary processor 64 are the time domain of the electrical sound signal. Filtering occurs on the time domain, and in the particular embodiment of FIGS. 1-19, on the digitized form of the time domain in the secondary processor 64. The frequency spectrums generated by the FFT in the primary processor 62 are the frequency domain of the sampled time segments of the time domain signal. Detection of resonating feedback frequencies is performed on the frequency domain in the primary processor 62.

Figure 2:
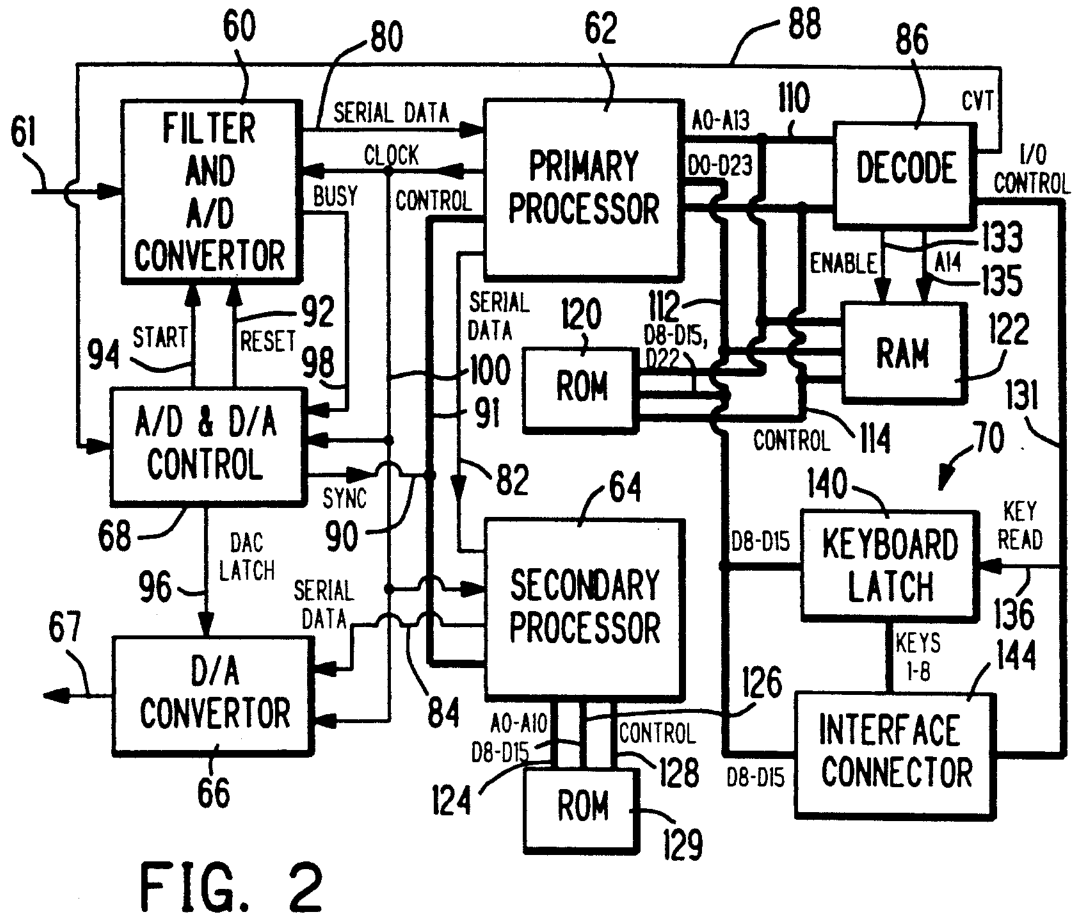
FIG. 2 is a more detailed block diagram of the adaptive resonant feedback filtering circuit of FIG. 1.

As illustrated in more detail in FIG. 2, a serial data line 80 connects the A/D convertor 60 to the primary processor 62; a serial data line 82 connects the primary processor 62 to the secondary processor 64; and a serial data line 84 connects the secondary processor 64 to the D/A convertor 66. The timing of serial word transmission is controlled by primary processor 62 including the use of a decoding circuit 86 to generate a signal CVT on line 88 applied to the control circuit 68. In response to the CVT signal on line 88, the control circuit 68 drives a sync line 90 in a serial control bus 91 joined to the primary and secondary processors 62 and 64 and drives reset and start lines 92 and 94 to A/D convertor 60 as well a DAC Latch line 96 to the D/A convertor 66 to control serial word transmission from the A/D convertor 60 to primary processor 62 and control the timing of expression of analog output from the D/A convertor 66. Busy signal line 98 is connected from the A/D convertor 60 to the control circuit 68 to time the completion of a serial word transmission cycle from the A/D convertor 60. A serial clock signal line 100 driven by the primary processor 62 is connected to the A/D convertor 60, the secondary processor 64, the control circuit 68 and the D/A convertor 66 to provide bit timing for the serial transmission of the digitized signal data. Serial transmission of the digitized sound signals and filter control signals over line 82 are controlled by the primary processor over the serial control bus 91. The conventional lines of the serial control bus 91 are illustrated in more detail in FIG. 5.

Figure 5:
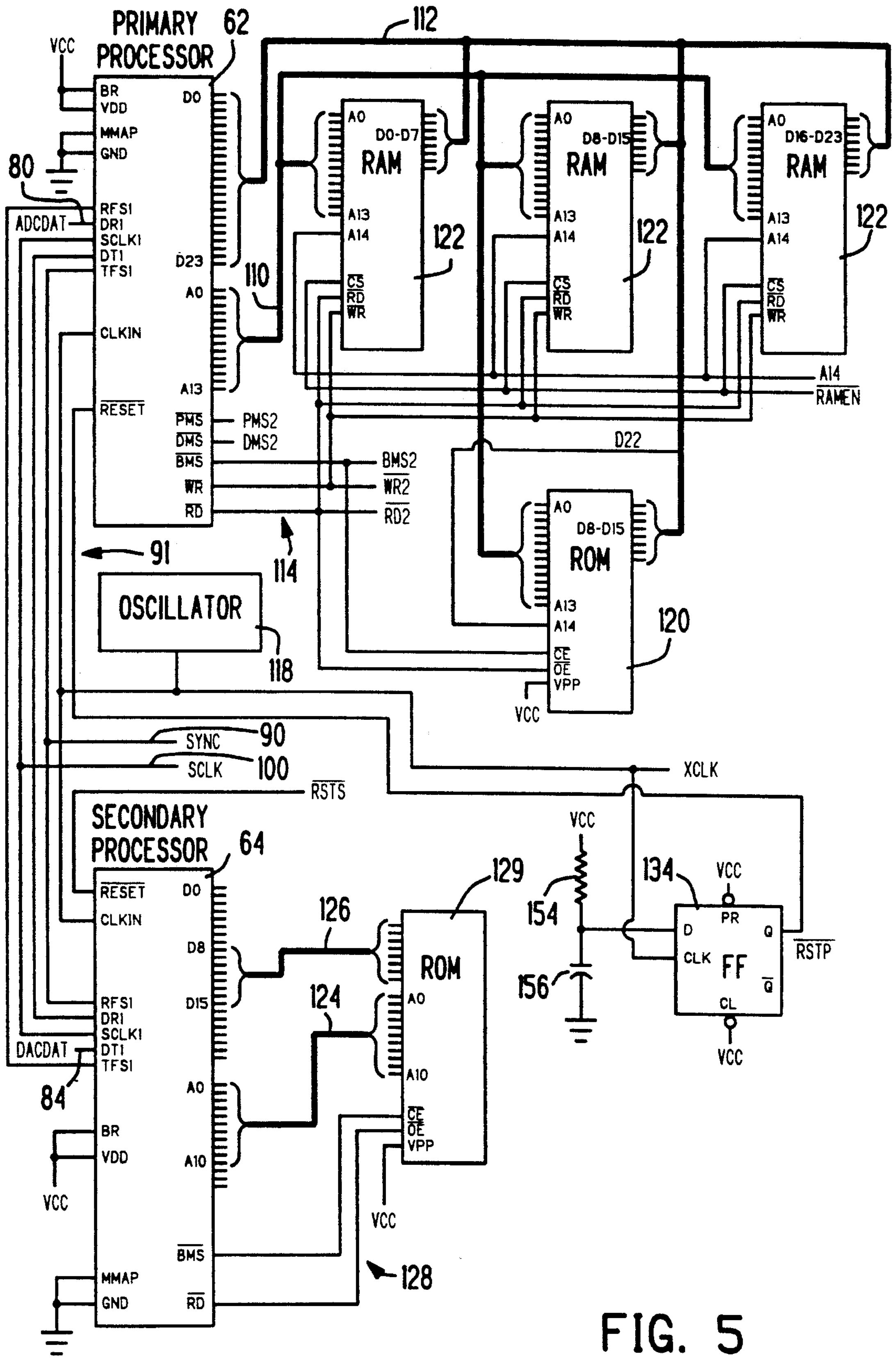
FIG. 5 is a detailed block diagram of primary and secondary processors with memory units of the circuit of FIG. 2.

The primary processor 62 is connected to an address bus 110, a parallel data bus 112 and a parallel control bus 114 which are all connected to ROM 120 and RAM 122. As shown in FIG. 5, the RAM 122 can be formed by parallel memory chips to provide a 24-bit parallel data path. Similarly the secondary processor 64 is connected by an address bus 124, a parallel data bus 126 and a parallel control bus 128 to a ROM 129. An external oscillator 118 is connected to clock inputs of the processors 62 and 64.

Figure 6:
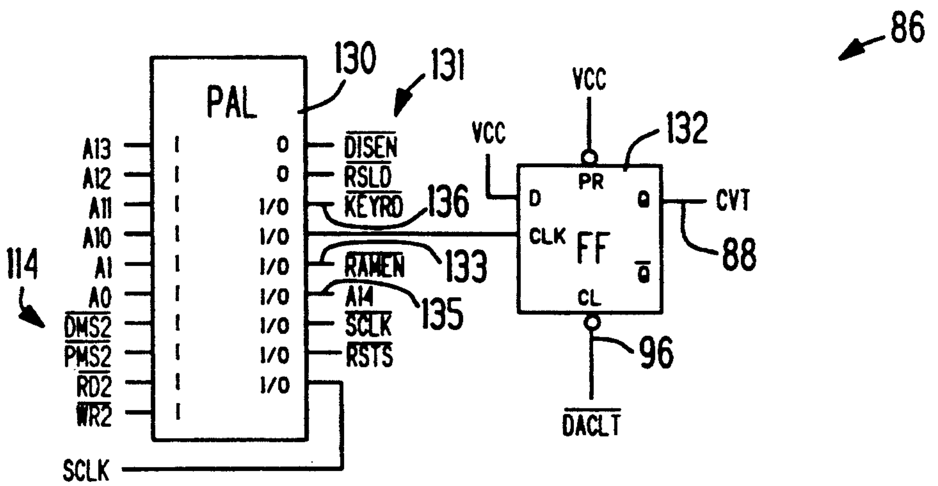
FIG. 6 is a detailed block diagram of a decode circuit in FIG. 2.

The address bus 110 and the control bus 114 are connected to the decode circuit 86 to generate various control signals on I/0 control bus 131, RAM enable line 133 and supplemental address line 135. The I/O control bus 131 operates the user interface 70 which includes a keyboard latch 140 and a connector 144. The latch 140 is controlled by a key read line 136 of the bus 131. As shown in FIG. 6, the decode circuit 86 includes a programmable array logic unit (PAL) 130 having inputs connected to the four most significant address lines and the two least significant address lines of the fourteen-bit address bus 110 along with the data (DMS2 ), program (PMS2 ), read (RD2 ) and write control (WR2 ) lines of the control bus 114. The back slash “ ” or the overhead line indicates an inverted signal. The following table illustrates the programming of the PAL 130:

TABLE I

PAL 130 Programming

| OUTPUT | INPUT X = DON'T CARE | | | | | | | | | |
|---|---|---|---|---|---|---|---|---|---|---|
| | A13 | A12 | A11 | A10 | A1 | A0 | $\overline{DMS2}$ | $\overline{PMS2}$ | $\overline{RD2}$ | $\overline{WR2}$ |
| DISEN | 1 | 1 | 0 | 1 | 0 | 0 | 0 | 1 | 1 | 0 |
| RSLD | 1 | 1 | 0 | 1 | 0 | 1 | 0 | 1 | 1 | 0 |
| KEYRD | 1 | 1 | 0 | 1 | 0 | 0 | 0 | 1 | 0 | 1 |
| C-CLK | 1 | 1 | 0 | 1 | 1 | 1 | 0 | 1 | 1 | 0 |
| RAMEN | 1 | 1 | 0 | 0 | X | X | X | X | X | X |
| A14 | 1 | 1 | 0 | 0 | X | X | 0 | 1 | X | X |
| RSTS | 1 | 1 | 0 | 1 | 1 | 0 | 0 | X | X | 0 |

The ROM 120 and the RAM 122 are larger than the maximum memory that can be addressed by a fourteen-bit address bus (16*k*). The high address output (A14) 135 is used to add another address bit to enable access to upper and lower memory portions containing data and program code, respectively. The RAMEN    output 133 supplies a control signal required by the memory chips. The output of PAL 130 connected to the clock input CLK of the flip-flop 132 is identified int he table as output C-CLK    and is used to trigger the flip-flop 132 to produce the CVT signal with the power phase and timing on the line 88. The duration of the CVT signal is determined by the DACLT    signal on line 96 form the PAL 130.

Figure 7:
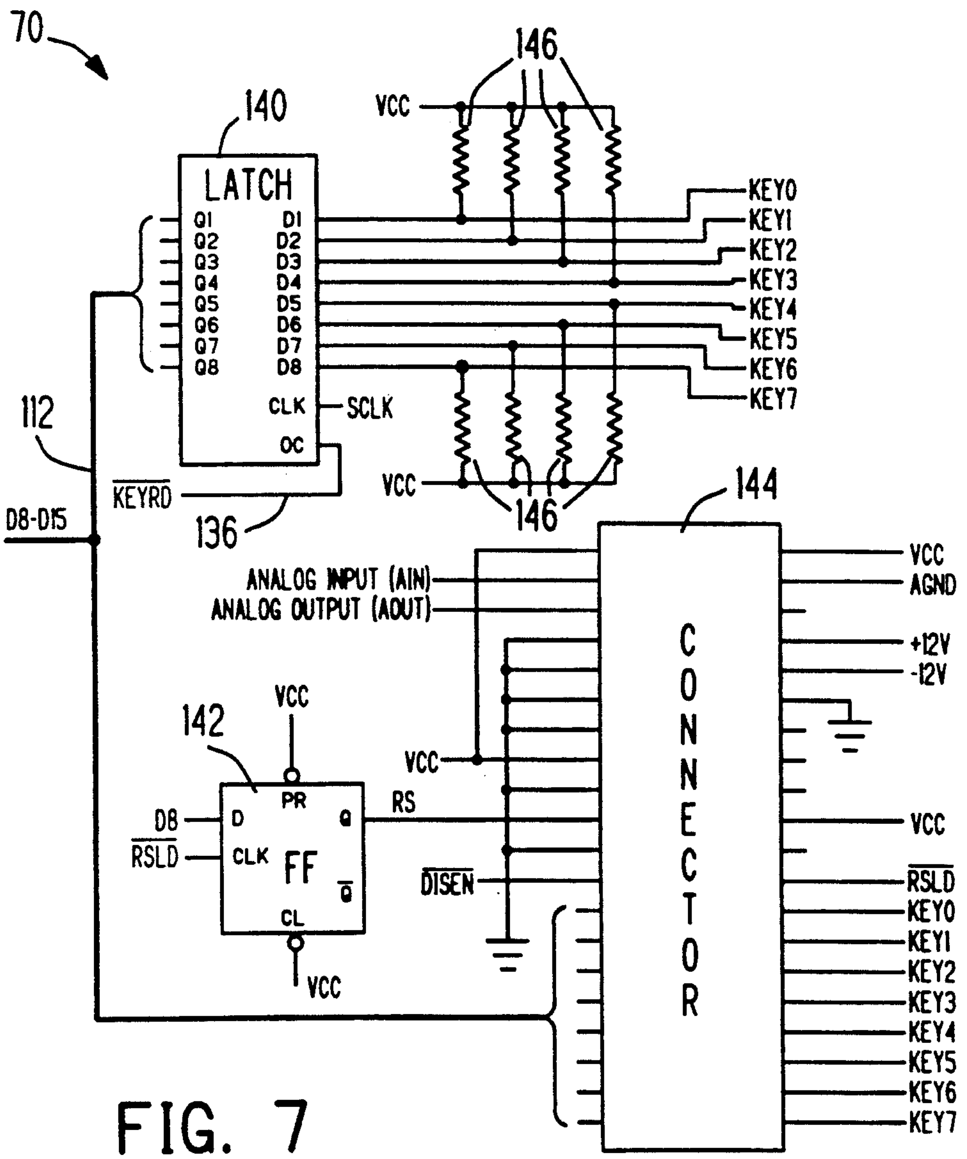
FIG. 7 is a detailed block diagram of a user interface circuit in FIGS. 1 and 2.

The outputs DISEN    , RSLD    and KEYRD    are connected to the user interface circuit 70 which as shown in FIGS. 2 and 7 includes a latch 140, a flip-flop 142 and a connector 144. The latch is connected by lines biased through resistors 146 and connector 144 to the keys of a conventional keyboard (not shown) to detect operation of a key. The flip-flop 142, the line DISEN and the data bus 112 are connected through the connector 144 to a LCD display (not shown) which is a conventional display operated in a conventional manner.

Additionally in FIG. 5, a resistor 154 is connected to the voltage source and one side of a capacitor 156 which has its other side connected to ground. The junction between the resistor 154 and the capacitor 156 is connected to the data input of a flip-flop 134 which is clocked by the external clock 118 to reset the primary processor 62 in a conventional manner upon power up of the circuit. The processor 62 during initialization resets the secondary processor 64 through PAL 130 and line RSTS    .

Figure 8:
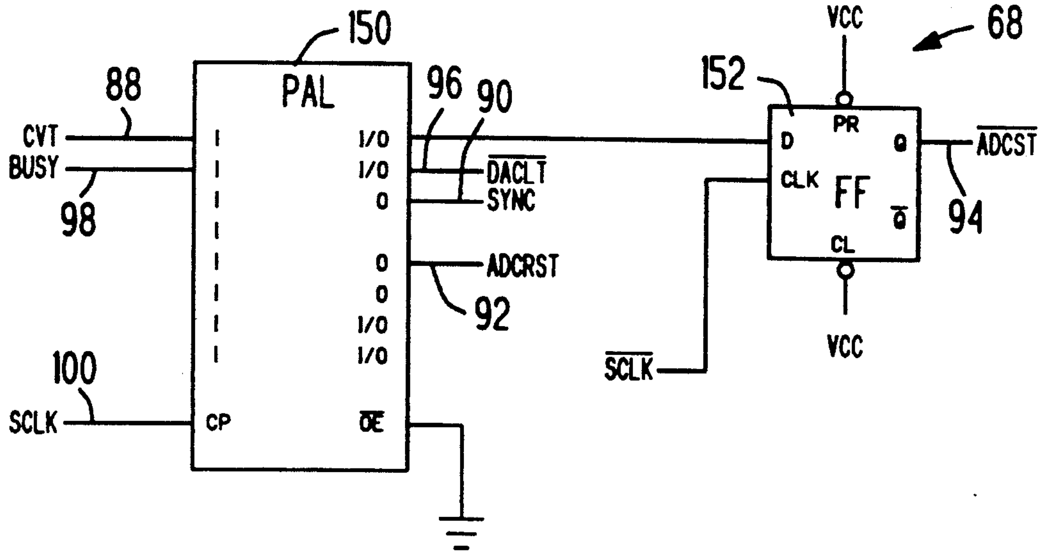
FIG. 8 is a detailed block diagram of a timing control circuit of FIG. 2.
Figure 9:
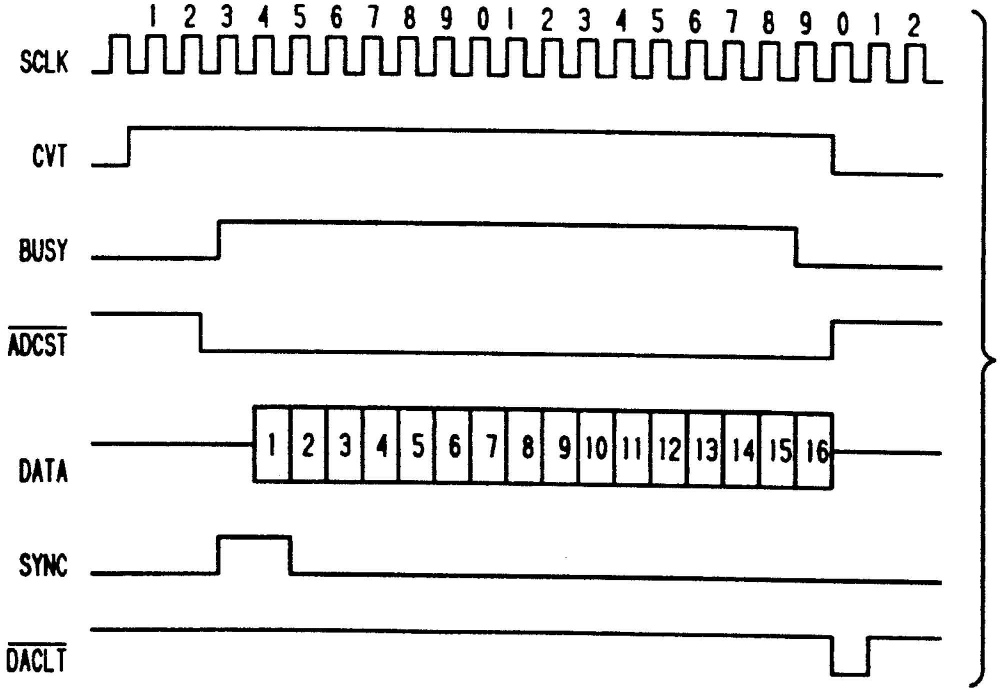
FIG. 9 is a chart of timing and control signal waveforms generated by various portions of the circuit of FIGS. 2 and 5–8.

Referring now to FIG. 8, the A/D & D/A control circuit 68 includes a programmable array logic unit 150 which has as inputs the CVT signal 88, the busy signal 98 and the serial clock signal SCLK. One output of PAL 150 is connected to a flip-flop 152 to provide the appropriate phase and timing for start signal ADCST on line 94. FIG. 9 illustrates the programming of the PAL 150 by showing the relative timing and duration of the ADCST    output as well as outputs DACLT    and SYNC on lines 96 and 90, respectively, as generated by the PAL 150 in a conventional manner from the inputs CVT, SCLK and BUSY. The relative timing and duration of the sixteen bit serial data streams passed on lines 80 and 84 are also represented in FIG. 9. The PAL 150 is programmed to generate the ADCRST output to reset the A/D convertor when the power is initially turned on.

Figure 10:
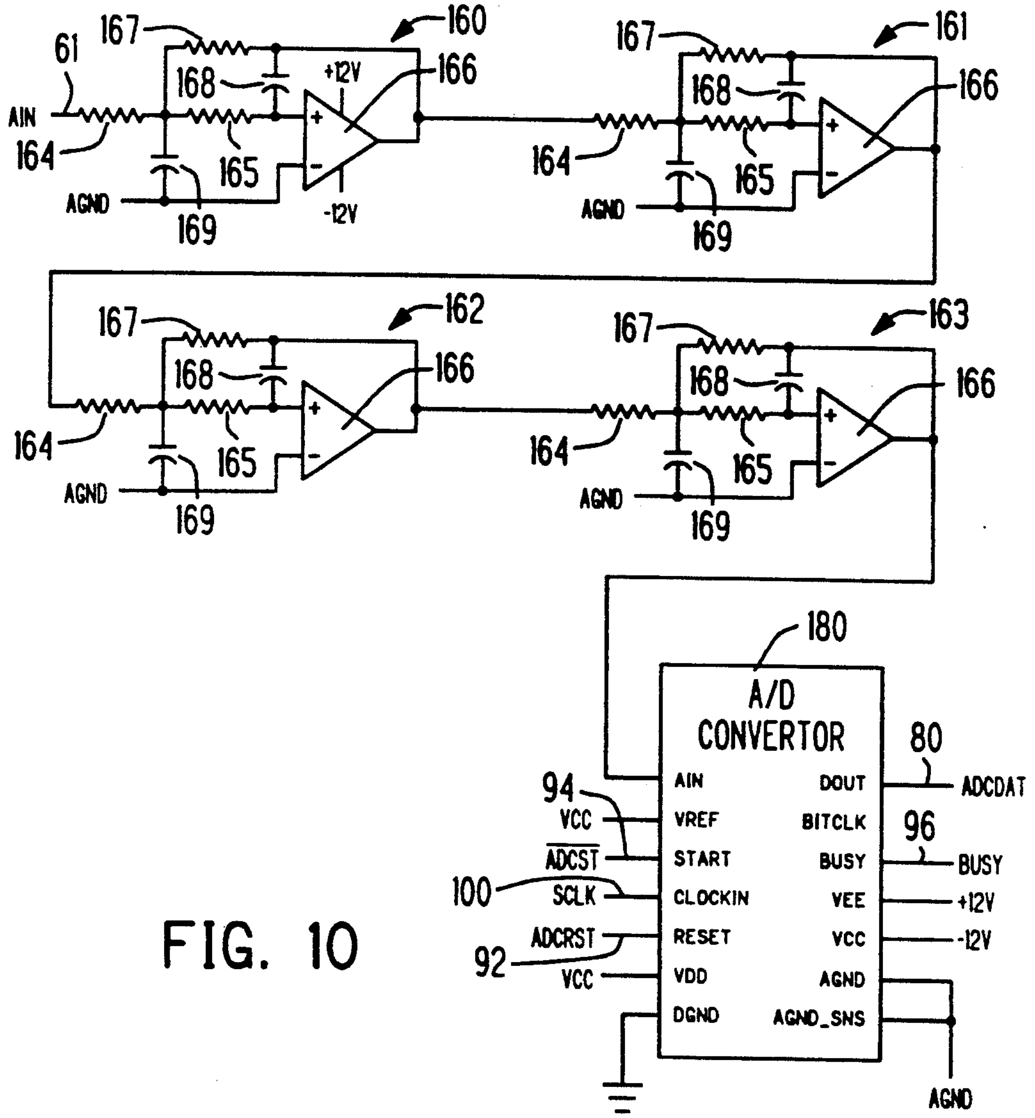
FIG. 10 is a detailed block diagram of a filter and analog-to-digital convertor circuit of FIG. 2.

The analog-to-digital circuit 60 is illustrated in FIG. 10 and includes conventional serially connected quad audio filter units 160, 161, 162 and 163 which receive the analog input signal on line 61. Each of the filter units includes input resistances 164 and 165, an operational amplifier 166, feed back capacitance 168 and resistance 167, and a filter capacitance 169. The output of unit 163 is connected to the input of a sixteen bit analog-to-digital convertor unit 180. A reference voltage input to the A/D unit 180 is supplied by the VCC. The filter units automatically adjust the direct current input level of analog input as well as filtering super-audio and sub-audio frequencies from the analog input.

Figure 11:
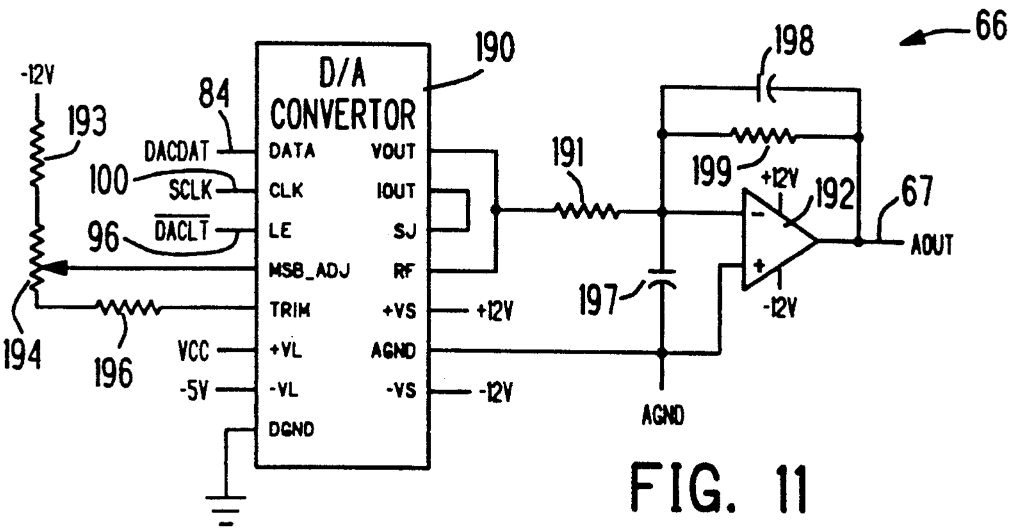
FIG. 11 is a detailed block diagram of a digital-to-analog convertor of FIG. 2.

The D/A convertor circuit 66 as shown in FIG. 11 includes a D/A convertor 190 which receives the incoming word on line 84 and produces an analog output applied through resistance 191 to the inverting input of an amplifier 192. Voltage control for the D/A unit 190 is provided by resistance 193, potentiometer 194 and resistance 196 connected to the +12 v supply. Capacitance 197 coupled across the inputs of the amplifier 192 and parallel feedback capacitance 198 and resistance 199 coupled across the output and inverting input of amplifier 192 provide for filtering of super-audio and sub-audio frequencies produced by the D/A convertor unit 190.

Figure 3:
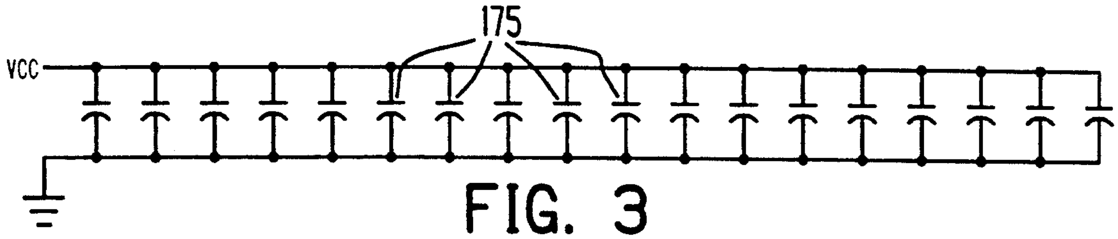
FIG. 3 is a circuit diagram of a power voltage filter used in the circuit of FIG. 2.
Figure 4:
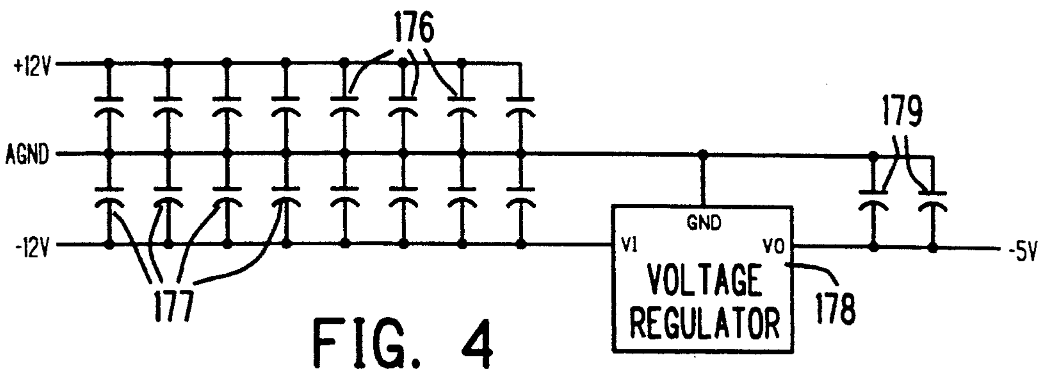
FIG. 4 is a circuit diagram of additional power voltage filter and generating circuits used in the circuit of FIG. 2.

FIG. 3 shows capacitors 175 for filtering the supply voltage VCC. FIG. 4 shows capacitors 176 and 177 for filtering the positive and negative twelve volt supplies. Voltage regulator 178 and capacitors 179 generate the negative five volt supply.

In one suitable example of the embodiment of FIGS. 1-11, the major components are listed in the following TABLE 11.

TABLE II

Major Components

| Unit | Model No. |
|---|---|
| A/D Convertor 180 | AD1876 |
| Processor 62 | ADSP2105 |
| Processor 64 | ADSP2105 |
| D/A Convertor 190 | AD1856 |

Figure 12:
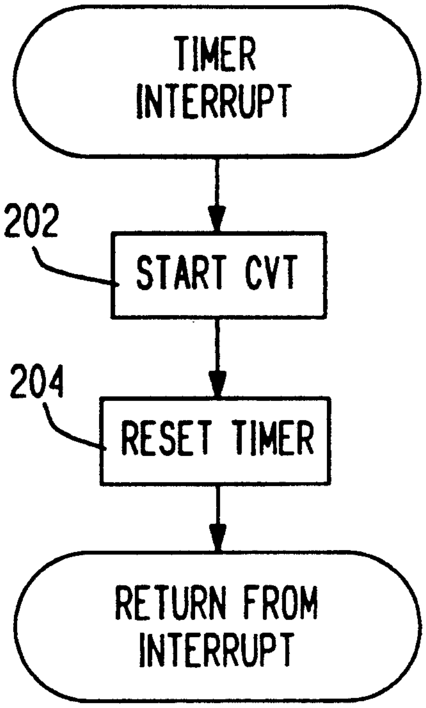
FIG. 12 is a program flow chart of a timer interrupt procedure for the primary processor of FIGS. 2 and 5.

The program for the primary processor 62 is illustrated in FIGS. 12, 13, 14, 15, 16 and 17. A timer interrupt program is shown in FIG. 12 wherein the decode circuit 86 is operated in step 202 to start the signal CVT which initiates transmission from the A/D convertor 60 to the primary processor 62 and from the secondary processor 64 to the D/A convertor 66. In step 204 the timer is reset. As an example, the CVT signal can be generated 45,000 times power second to result in a Nyquist frequency of 22.5 KHz.

Figure 13:
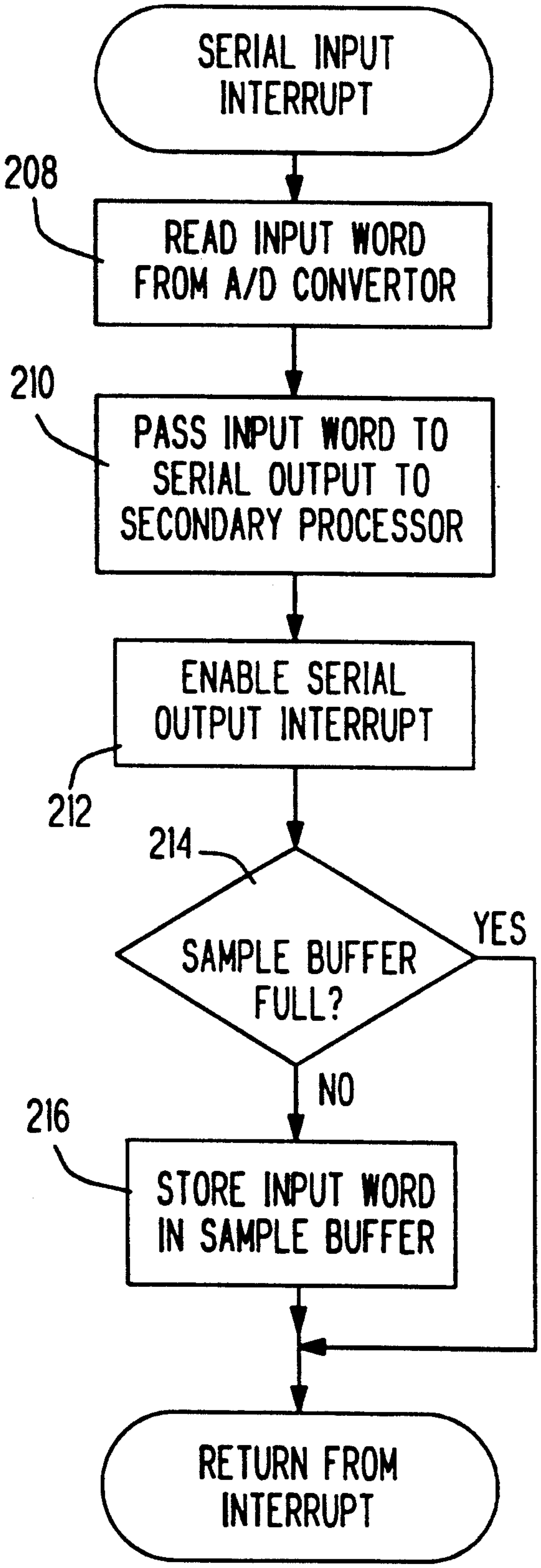
FIG. 13 is a program flow chart of a serial input interrupt procedure for the primary processor of FIGS. 2 and 5.

When an incoming serial word has been received by the primary processor 62, the interrupt procedure of FIG. 13 is called. The word is read in step 208 and passed to the serial output device in step 210 for transmission to the secondary processor 64. In step 212, a serial output interrupt is enabled so that the processor 62 can transmit a control filter word after transmission of the data word is completed. In step 214, the program determines if a sample buffer is full, and if not, the data word is stored in step 216 in the sample buffer. With the buffer set up to receive 4096 data points, the buffer receives about a 0.09 second time segment of the input signal. The program then executes a return from interrupt.

Figure 14:
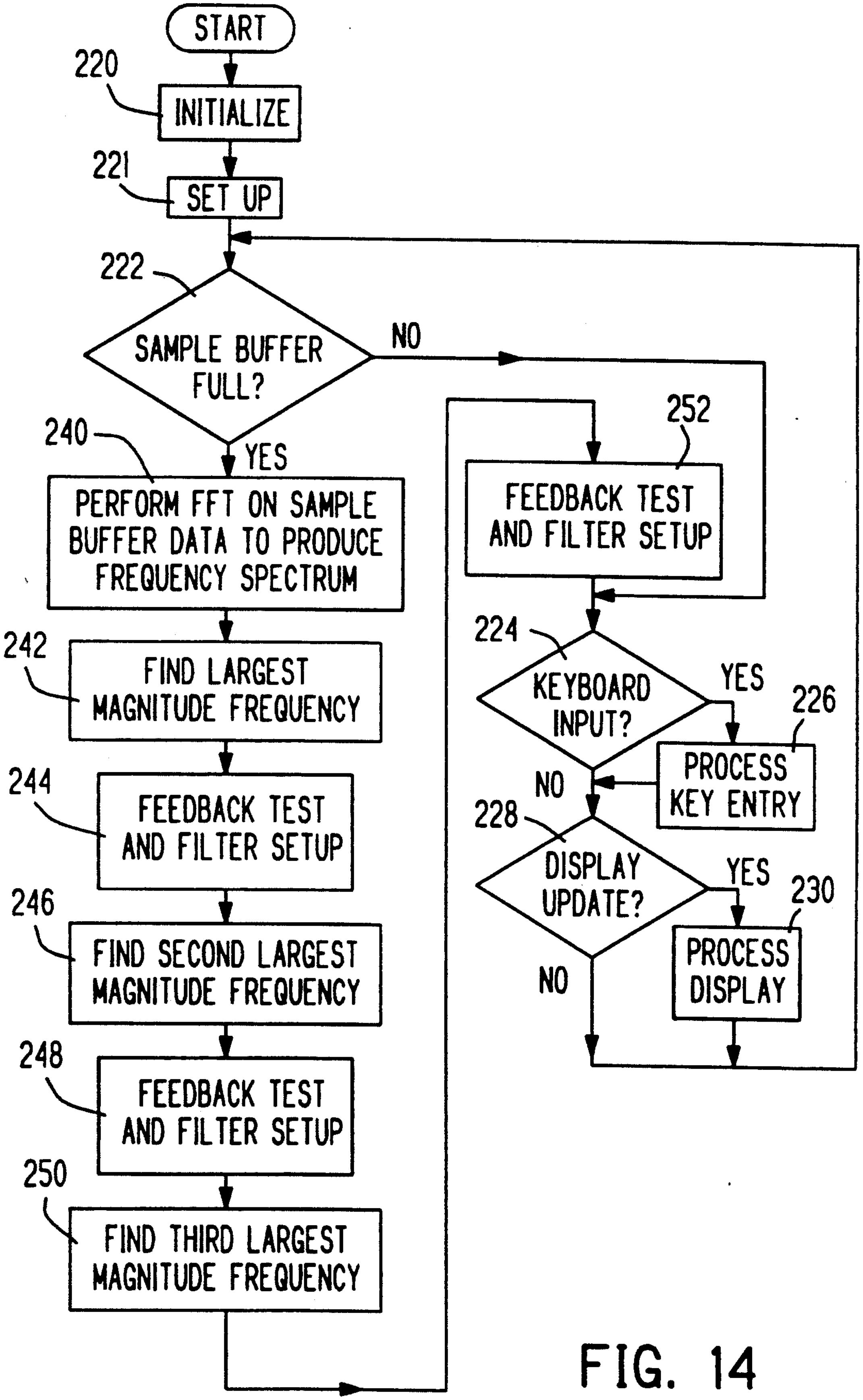
FIG. 14 is a program flow chart of a main operating program used in the primary processor of FIGS. 2 and 5.

The main operating program for the processor 62 is shown in FIG. 14. Upon power up the program in step 220 initializes all the hardware as well as loading the program and data tables from the ROM 120 into the RAM 122. Next, the program in step 221 sets up filters for any resonating feedback frequencies that can be uncovered in the set up procedure. In step 222 the program determines if the sample buffer is full. If not, the program proceeds to step 224 where any keyboard input would be loaded by branching to step 226 and then to step 228 where updating of the display device (not shown) would occur by branching to step 230. From step 228 or step 230 the program returns to step 222.

Once the sample buffer is full, for example has received 4096 words, the program in step 222 branches to step 240 where a Fast Fourier Transform (FFT) is performed on the data in the sample buffer. For example, the program can perform a conventional 4096 point FFT with a resolution of 10.755 Hz over the frequency range from zero to the Nyquist frequency. The frequency spectrum generated by the FFT is normalized. Then in the following steps 242, 244, 246, 248, 250 and 252, the program finds and analyzes the three largest magnitude frequencies in the frequency spectrum generated by step 240. This analysis can be limited to the most pertinent portion of the audio spectrum, for example from 60 to 15,000 Hz. First the largest magnitude frequency is found in step 242. Then in step 244 a feedback and filter setup procedure is performed.

Figure 15:
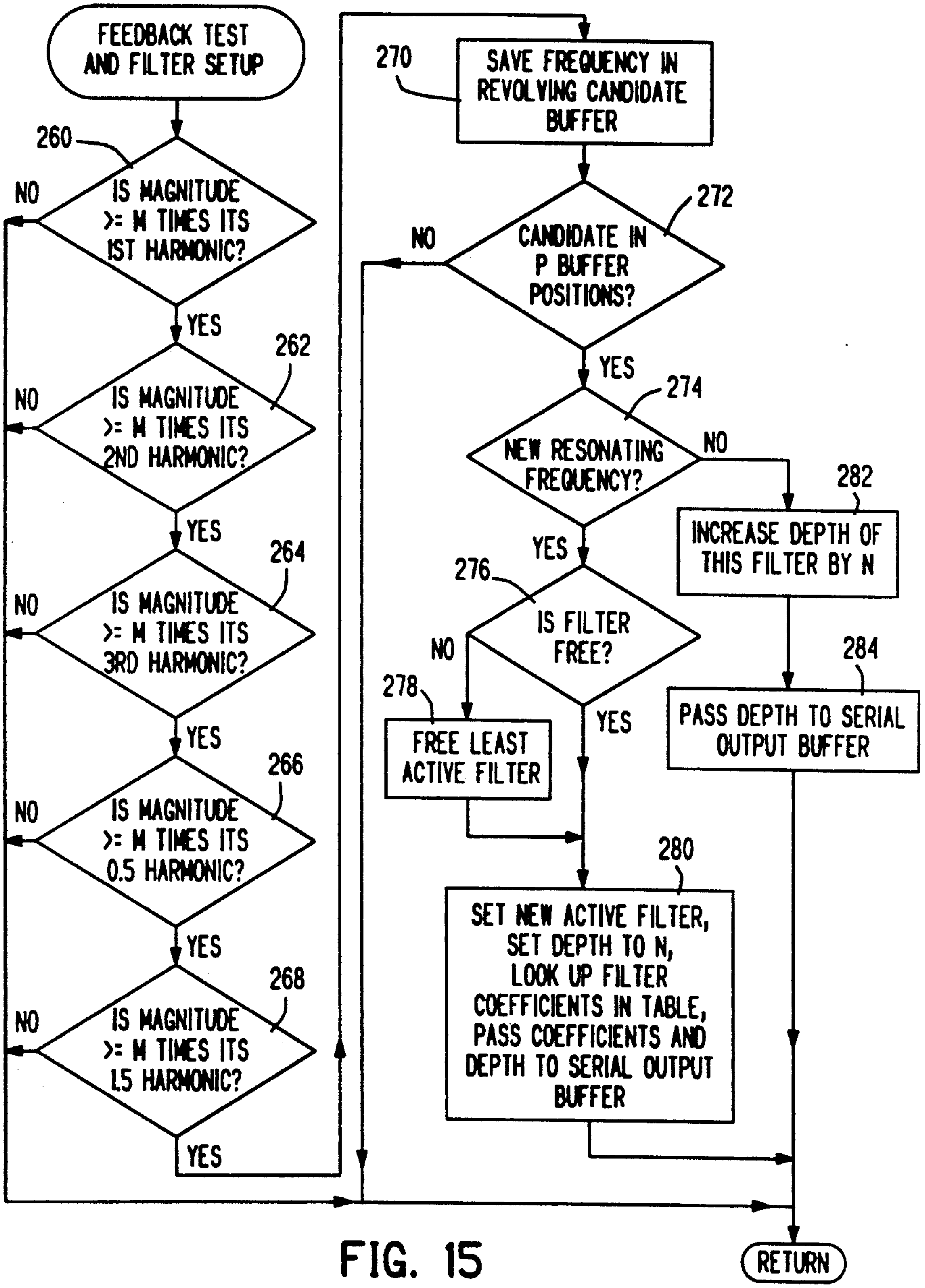
FIG. 15 is a program flow chart of a feedback test and filter setup procedure called by the main operating program of FIG. 14.

This feedback and filter set up procedure is shown in FIG. 15 and includes steps 260, 262, 264, 266 and 268 where the magnitude of the frequency being analyzed is compared to various harmonics and subharmonics of the frequency being analyzed. For example, the relative magnitude of the 1st, 2nd, 3rd, 0.5 and 1.5 harmonics can be determined. If the magnitude of the frequency being analyzed is equal to or greater than M times each of these harmonics or subharmonics, then the frequency is determined to be a candidate for being a resonating feedback frequency. The value M can be the same or different for each of the tested harmonics and subharmonics, for example the frequency under test is a feedback candidate if it is at least 33 dB greater than its closest harmonics and subharmonics. If the frequency being analyzed fails any of the tests 260, 262, 264, 266 or 268, the program returns to the procedure of FIG. 14.

When a frequency is identified as a candidate feedback frequency, the program in step 270 of FIG. 15 places this frequency in the current position of a revolving candidate buffer. Then in step 272 it is determined if this frequency is stored P times in this buffer where P is an integer equal to or greater than two. For example the buffer can include five positions or frequency storage locations for each of the three frequencies being analyzed, and if the frequency occurs in three of these positions, corresponding to the frequency being one of the three largest magnitude frequencies in three out of five successive frequency spectrums, the frequency under analysis is identified as a resonating feedback frequency. Then step 274 determines if this resonating feedback frequency is a new feedback frequency or has been previously identified. The program can control a plurality of notch filters, such as twelve filters, and the depth and frequency of each of these filters as well as whether the filter is fixed, not in use or in use are stored in memory. If it is a new feedback frequency, the program proceeds to step 276 where it is determined if there are any free filters, i.e. any that are not in use. When all twelve filters are being used, the program in step 278 determines the oldest non-fixed frequency and frees this filter. From step 276 if true or from step 278, the program proceeds to step 280 where a new filter is set to the new feedback frequency, and the new depth is set to N in the range generally from one to forty dB, preferrably in the range from one to six dB, and in most cases 3 dB or less. Also, the filter coefficients are looked up in a table previously stored in RAM, and target addresses, the coefficients and the depth are passed to a circular coefficient output buffer. Back in step 274 when the feedback frequency is found to have previously existed, the program in step 282 increases the depth by N, and then in step 284 passes only the target address and depth to the output buffer.

After the feedback test and filter setup for the largest magnitude frequency, the program in FIG. 14 similarly analyzes the second largest and third largest magnitude frequencies. The processor 62 can receive and analyze from two to five time segments of the input signal per second; in one example the processor receives and analyzes about four time segments per second wherein each time segment contains 4096 points of the input signal collected over a time period of about 0.09 seconds.

As an alternative to employing only a single FFT in step 240, the program can intermittently perform multiple FFTs, such as two or three FFTs, covering the lower and intermediate portion of the audio spectrum with a higher resolution. With two FFTs, the data in the sample buffer can be filtered to eliminate frequencies above 5000 Hz. Then every fourth word in the buffer is averaged with three adjacent words to produce a 1024 point sample buffer which is subjected to the second FFT at a resolution in the range from 1 to 3 Hz, such as 2 Hz. The normalized frequency spectrum generated by this second FFT is then analyzed over the lower range, for example 60 to 1000 Hz, of the audio spectrum. In the steps 242, 244, 246, 248, 250 and 252, the higher resolution of the second FFT would enable more accurate positioning of the notch filtering frequencies in the lower frequency range. For three FFTs, three 1024 point FFTs, with appropriate filtering and averaging, can be performed over the ranges 60 to 650 Hz, 650 Hz to 2.5 KHz, and 2.5 to 15 KHz with resolutions of 2.5 Hz, 10 Hz and 40 Hz, respectively. This will produce an accuracy of one-fiftieth of an octave in placement of the filters.

Figure 16:
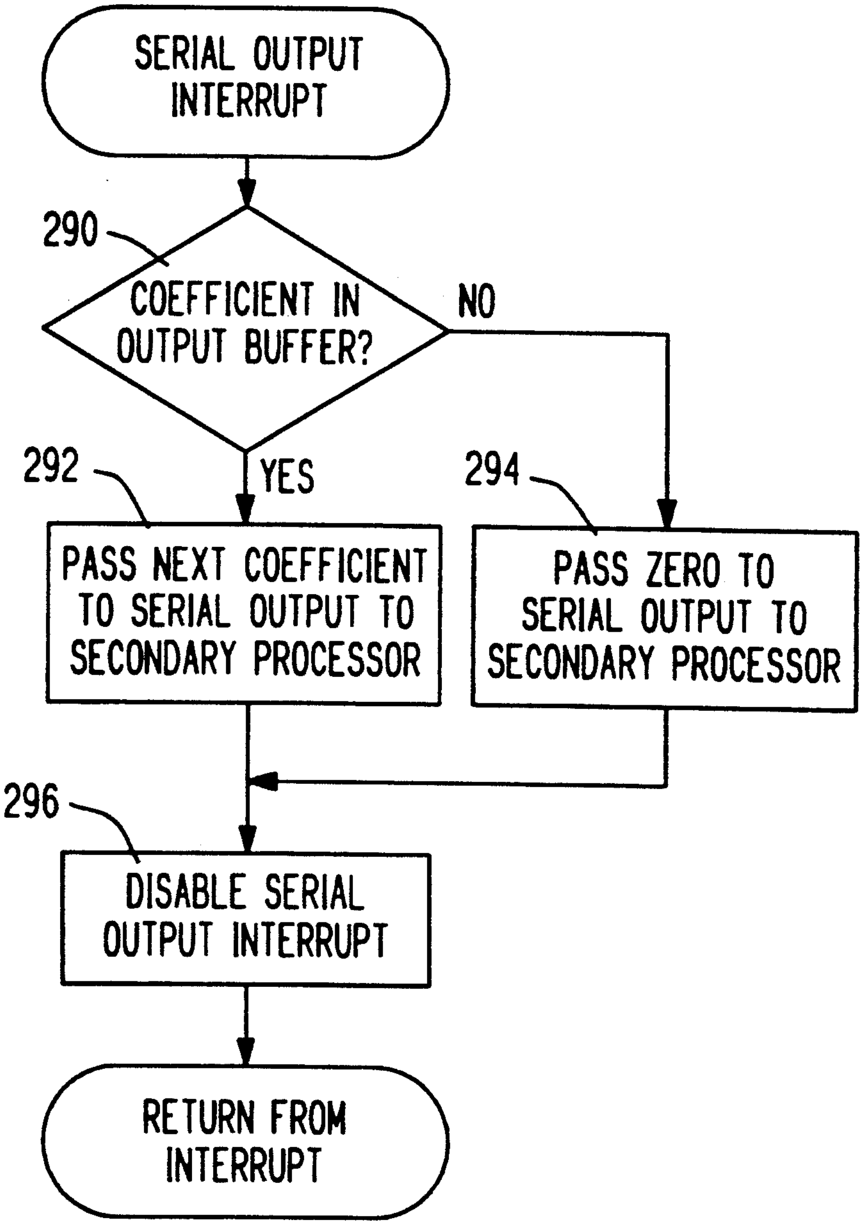
FIG. 16 is a program flow chart of a serial output interrupt procedure of the program in the primary processor of FIGS. 2 and 5.

The primary processor 62 transmits target addresses, filter coefficients, and depths to the secondary processor 64 by alternating coefficient output buffer words with the time domain signal data words being transmitted to the secondary processor 64. When transmission of a data word is complete, the serial output interrupt procedure of FIG. 16 is called. In step 290, it is determined if address words, coefficient words or any depth words remain in the circular buffer for transmission. If true, the next address word, coefficient word or depth word is transferred in step 292 to the serial output device of the primary processor 62 for transmission to the secondary processor 64. Otherwise when step 290 is false, a zero is transferred in step 294 to the serial output. Then in step 296 the serial output interrupt is disabled so that next following word transmitted will be a data word by the procedure of FIG. 13.

Figure 17:
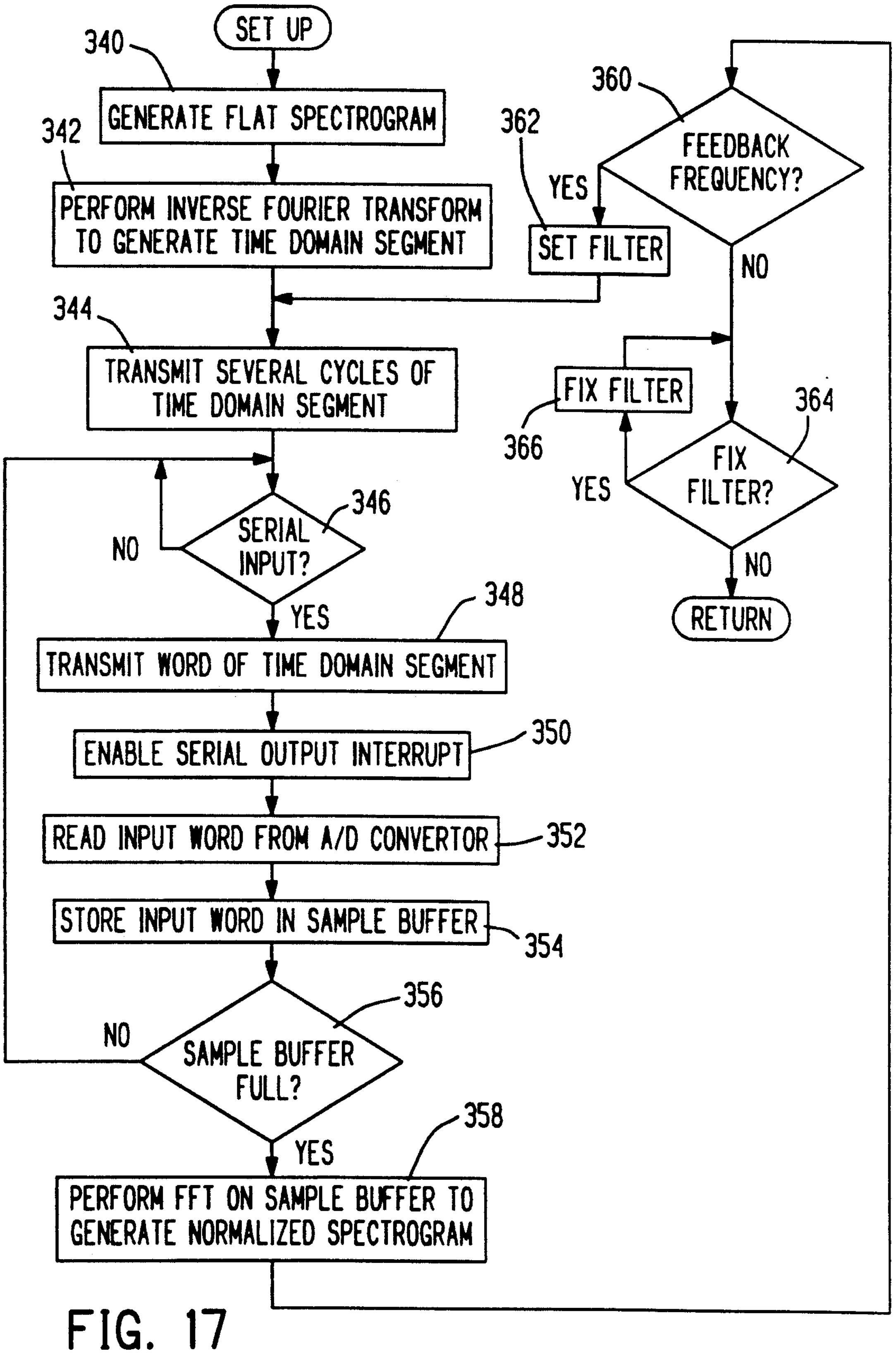
FIG. 17 is a program flow chart of a set up procedure used at the beginning of the main program of FIG. 14.

The set up procedure for initially determining and setting resonating feedback frequencies is shown in FIG. 17. This occurs after the initial power up of the amplifier system. In step 340, the processor 62 generates a flat spectrogram or frequency spectrum. Then in step 342, this spectrogram is subjected to an Inverse Fourier Transform (IFT) to generate a series of digital words defining a time domain segment of noise. Several cycles of this time domain segment are transmitted to the secondary processor 64 in synchronism with the CVT signal operating the A/D convertor in order to saturate the room with sound waves of the noise. Then in step 346, the presence of a serial input is tested until the input of a serial word from the A/D convertor is indicated. When the serial input of a word is completed, the program proceeds to step 348 where a word from the time domain generated by the IFT is transmitted to the secondary processor for filtration and transmission to the secondary processor. The serial output interrupt is enabled in step 350 so that the procedure of FIG. 16 is called upon completion of the data word transmission to transmit a word from the coefficient buffer. The serial input word is read in step 352 and stored in the sample buffer in step 354. In the step 356 the procedure returns to the step 346 until the sample buffer is full. Once the sample buffer is full, the program branches from step 356 to step 358 where a FFT is performed on the sample buffer data to generate a normalized frequency spectrum. Then in step 360, it is determined if any resonating feedback frequency is present in the spectrum by cross-spectral comparison with the flat frequency spectrum generated in step 340. When one or more resonating feedback frequencies are found, a filter is set in the same manner as in step 280 of FIG. 15 and the program returns to step 344 until all resonating feedback frequencies are normalized. Once any resonating feedback frequency or frequencies are normalized, the program proceeds to step 364 where the operator is given the opportunity to designate each of the filters, as set in step 362, up to a predetermined maximum such as nine, as fixed filters. The number of fixed filters can vary from three up to two or three less than the total number of filters. Fixed filters can not be freed by the procedure of step 278 but will remain active until the power to the system is turned off. After the operator has indicated by the keyboard the fixing or declining to fix any filters up to the maximum number of allowed fixed filters, the program of FIG. 17 returns to the procedure of FIG. 14.

Figures 18, 19:
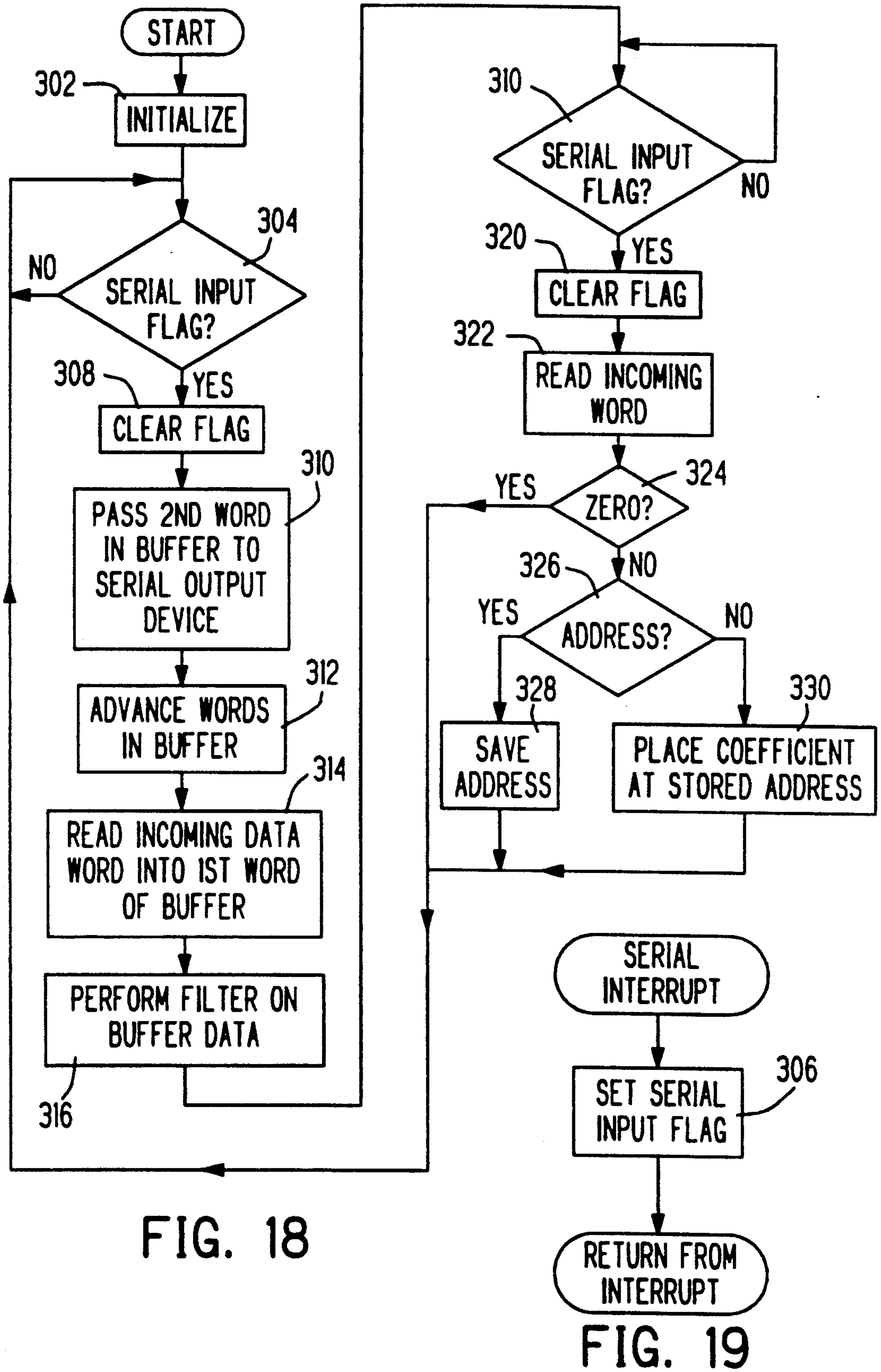
FIG. 18 is a program flow chart of a main operating program used in the secondary processor of FIGS. 2 and 5.
FIG. 19 is a program flow chart of a serial input interrupt procedure used in the secondary processor of FIGS. 2 and 5.
Figure 20:
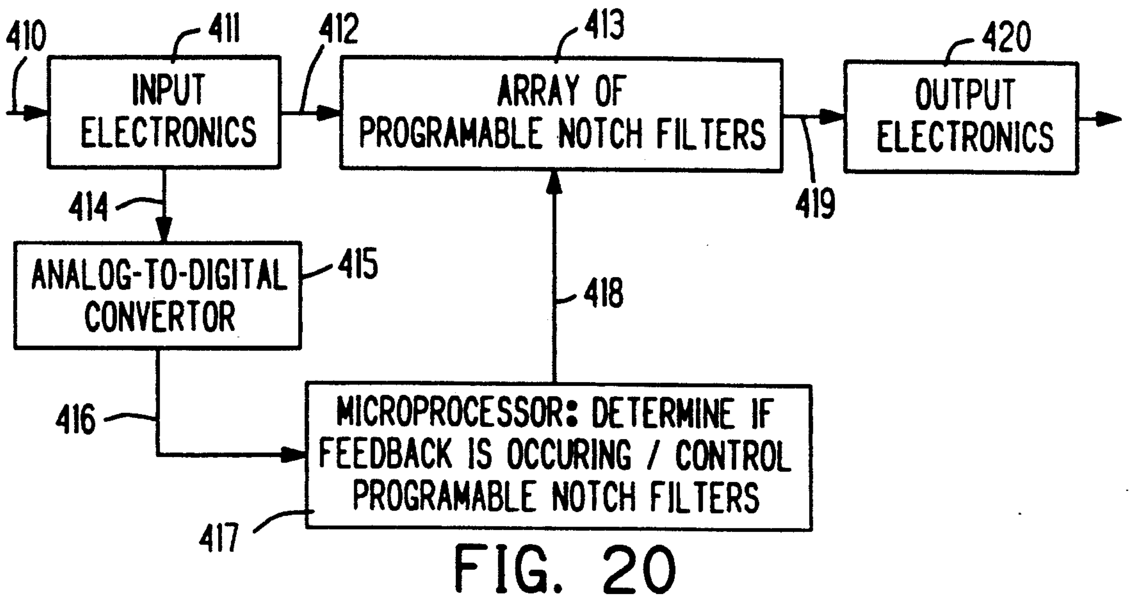
FIG. 20 is a block diagram of a modified adaptive resonant feedback filtering circuit in accordance with the invention.

The program for the secondary processor 64 is illustrated in FIGS. 18 and 19. Upon power up the program in step 302 of FIG. 18 initializes all hardware and loads the program from ROM 129 into internal RAM of the processor 64. In step 304, the program waits for a serial input flag which is set in step 306 of FIG. 19 when a word has been received by the serial input device of the processor 64. Then in steps 308 and 310, the flag is cleared and the second word in the filter buffer is transferred to the output device of the processor 64. The program then proceeds to step 312 where the words in the filter buffer are advanced and to step 314 where the incoming word is transferred into the first word location in the filter buffer. A conventional filter algorithm, such as a Butterworth Infinite Impulse Response filter algorithm with a filter length of two is performed in step 316. This algorithm attenuates the twelve filter frequencies in accordance with the previously received filter coefficients. The number of filters can be changed to any other desired number, such as nine, etc. The filter coefficients stored in the table of the ROM 120 of the processor 62 were created by conventional means so as to produce notch filtering of a width from one-fourth to one-thirtieth of an octave, such as one-tenth of an octave.

After the filter buffer data has been filtered, the program proceeds to step 318 where the serial input flag is again tested. If false, the program continues to cycle through step 318 until the flag becomes set by step 306. When true, the flag is cleared in step 320 and the incoming word is read in step 322. If this word is zero indicating no change in the filtering algorithm, the program in step 324 returns to step 304. If the word is not zero, it is either an address, a filter coefficient or a filter depth. A target address must be received first by the processor 64 for each filter coefficient and depth word so that the program in step 326 branches to step 328 and saves the address. Then in the next cycle through the procedure of FIG. 18, the program in step 326 branches to step 330 to place the filter coefficient or depth value at the address stored in step 328. After a zero, the program in step 326 knows that the next non-zero word will be an address with subsequent words alternating between coefficient or depth words and address words. In this manner the filter is adapted to changing feedback conditions to filter the feedback frequencies with minimum distortion of the sound.

In a variation of the adaptive filtering system shown in FIGS. 20, 21, 22, 23, 24, 25 and 26, an input signal 410 from one or more microphones or a PA mixer is applied to an input electronic circuit 411 wherein the signal is preamplified and/or mixed. The analog signal is passed over line 412 to an array of programmable notch filters 413, for example six switched capacitor filters which filter the analog form of the time domain signal as an alternative to the embodiment of FIGS. 1-19 filtering the digital form of the time domain signal. The analog signal from the circuit 411 is also directed over line 414 to an analog-to-digital convertor 415. The digital signal 416 from the analog-to-digital convertor is fed to a microprocessor 417 wherein the signal is periodically sampled to determine if feedback is occurring in the range of frequencies being monitored. The microprocessor is software based and uses a Fast Fourier Transform to generate a frequency spectrum which is then analyzed to determine whether or not a feedback is present at any given frequency. If feedback is determined, the microprocessor emits control signals 418 to the array of programmable notch filters 413 to set up one or more filter notches to attenuate the detected feedback frequency or frequencies. Thereafter, the filtered output 419 which has been attenuated at the selected frequencies is fed to an output electronic circuit 420 wherein the voltage level of the signal is reset to the same level as entering into the input electronic circuit 411.

Figure 22:
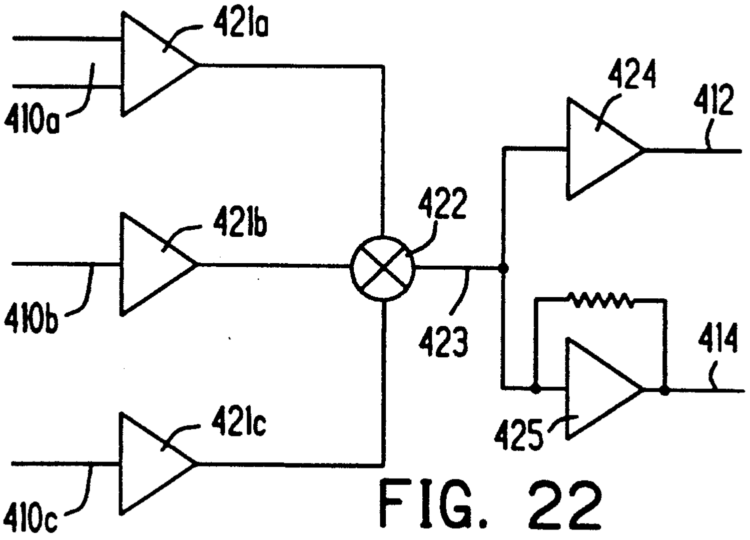
FIG. 22 is a circuit diagram of an input portion of the circuit of FIG. 20.

Referring to FIG. 22, one example of the input electronic circuit 411 is disclosed wherein the input 410 is a plurality of different sources such as a plurality of microphones. The incoming signals, shown as 410*a–c*, are first amplified through amplifiers 421*a–c* with the signals being thereafter mixed in a conventional mixer 422 from which the output signal 423 is split with the first portion of the signal passing through a buffer amplifier 424 to obtain the output signal 412 which is directed to the array of programmable notch filters 413. The second portion of signal 423 passes through a variable gain amplifier 425 wherein the analog signal may be favorably adjusted with the output 414 being directed to the analog-to-digital convertor 415. Various other arrangements of mixers and/or preamplifiers can be used in place of the circuit of FIG. 22. The input electronics are provided in order to adjust the incoming program signals to the appropriate voltage levels so as to be compatible with the remaining portion of the electronic circuits associated with the equalizer.

Figure 23:
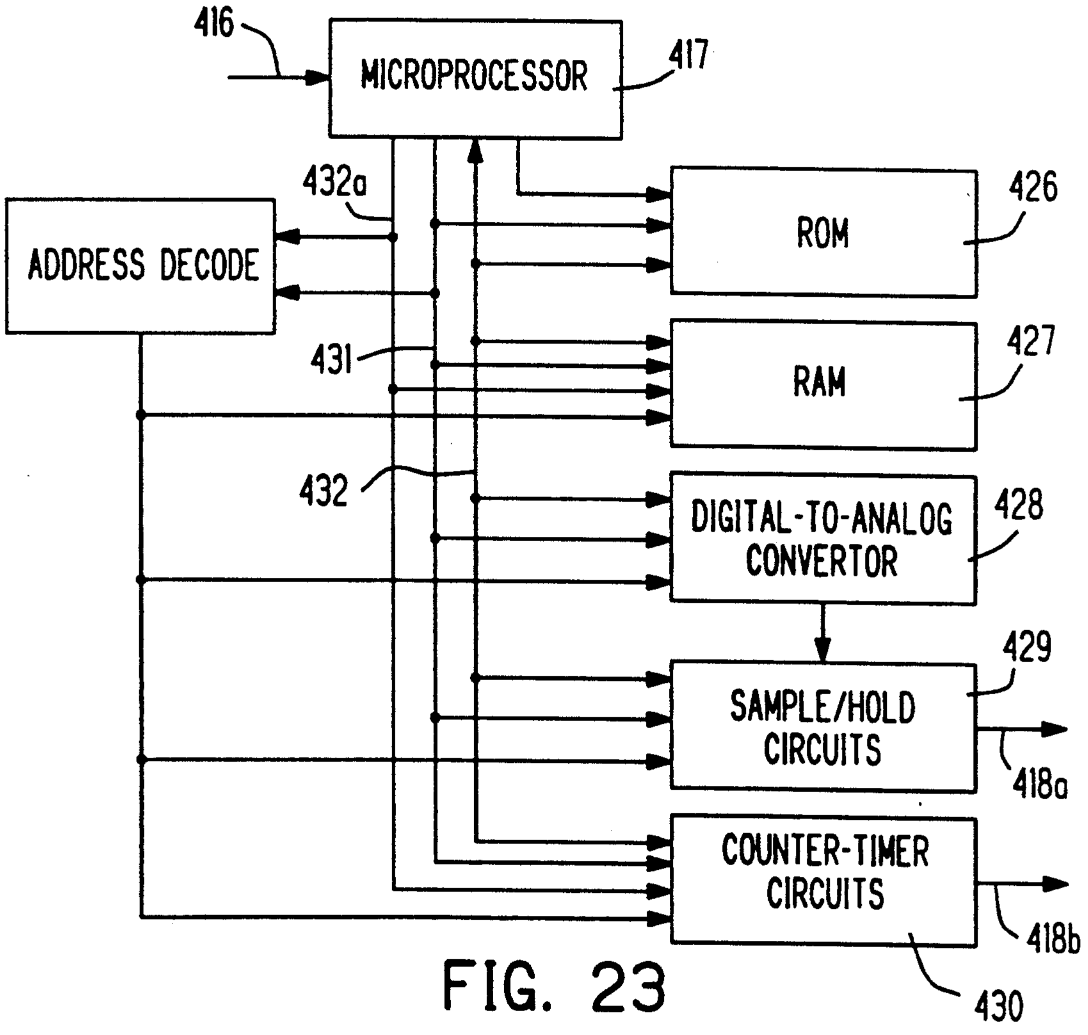
FIG. 23 is a detailed block diagram of a microprocessor circuit of the circuit of FIG. 20.

In FIG. 23, the digital output 416 from the analog-to-digital convertor 415 is received by the microprocessor 417. The microprocessor is software based and includes a read only memory (ROM) 426, a random access memory (RAM) 427, a digital-to-analog convertor 428, a series of sample and hold circuits 429 (the number of which are equal to the number of programmable notch filters) and counter timer circuits 430 (also coinciding in number with the number of programmable notch filters). Each of the elements of the microprocessor are connected through an address bus 431, data bus 432 and a control bus 432*a* as is shown. The particular details of the microprocessor may of course be varied and still obtain the necessary sampling, assigning and control circuit functions.

It is the purpose of the microprocessor to sample the incoming digital data to determine at which frequencies in the audio program resonances are being developed. When the equalizer is placed within a given area or room, once the unit is activated or energized, it has been found that there will be a number of resonant frequencies initially detected which are indicative of the configuration of the room and its natural acoustics. As the microprocessor samples the incoming signals it automatically assigns such resonant frequencies to the array of programmable notch filters 413 in the order in which they are received. It has been found through testing that once an initial number of resonant frequencies has been established upon the activation of the equalizer, that these initial resonant frequencies should be continuously filtered and therefore a given number of the notch filters are locked or dedicated to those frequencies. Therefore, the software associated with the microprocessor will automatically ensure that a first given number of notch filters are locked to such frequencies. The program automatically functions to release the dedicated notch filters in the event the equalizer is deenergized.

For example, the first three filters can be considered dedicated filters such that when the first three resonant frequencies are identified by the microprocessor these dedicated filters are set to create notches at the detected feedback frequencies and will retain such frequency notches throughout the period in which the amplifying system remains operative. For purposes of identification and example, attention is directed to FIG. 24 wherein the first three filters, indicated at 413*a*, 413*b*, and 413*c*, are considered the dedicated filters.

During the normal operation of the amplifying system, the microprocessor 417 continues to sample the incoming digital data, and if additional resonant frequencies are identified, the control signal 18 from the microprocessor controls the remaining filters 413 to create notches in the additional resonant feedback frequencies. For example when a fourth resonating feedback frequency is detected, the microprocessor 417 controls notch filter 413*d* of FIG. 24 to attenuate the fourth feedback frequency.

In some instances, more than six resonating feedback frequencies may be encountered. If this occurs, the resetable filters, 413*d*–413*f*, are reassigned by the microprocessor which determines which of the additional resonant frequencies, i.e. those received after the initial three, are to be filtered by the resetable filters 413*d*–413*f*. Thus, the frequencies at which notches are created during a performance amplified by the amplification system can vary depending upon the resonating frequencies detected by the microprocessor. The software associated with the microprocessor selects those frequencies which would be most disruptive to the amplified sound to assign to the available filters.

Figure 21:
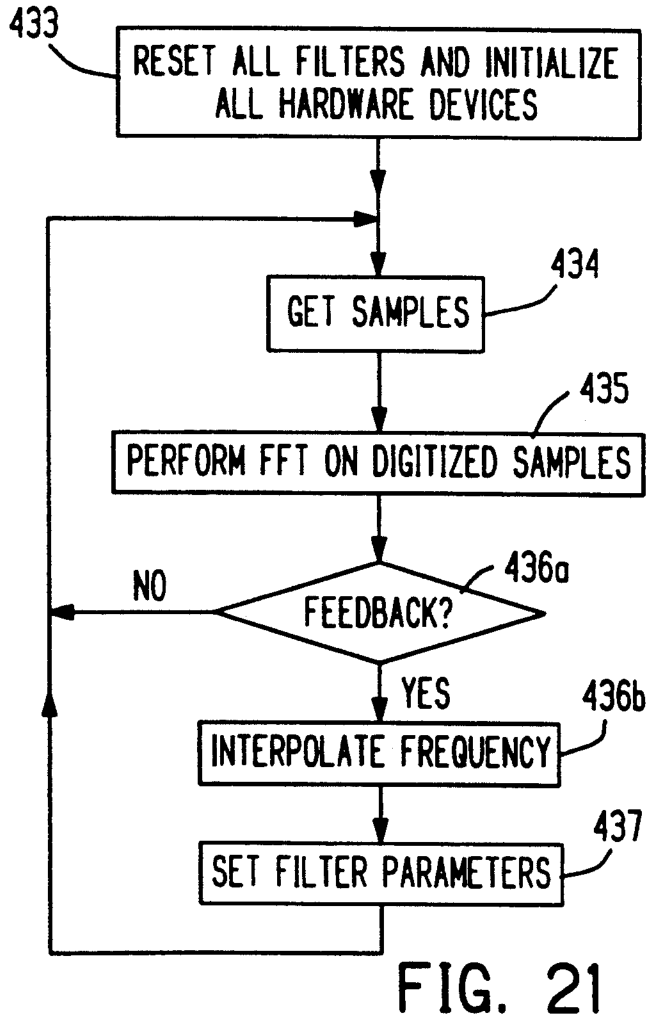
FIG. 21 is a program flow chart of a program used in the microprocessor in the circuit of FIG. 20.

In FIG. 21, a flow diagram of the software begins with step 433 where all filters are reset and all hardware devices are initialized. During normal operation, samples of the digitized signals are taken and held in a RAM by step 434. The number of samples is determined by the number required by the FFT to be performed in step 435. Samples may be collected in separate low and high frequency buffers for testing high and low frequency ranges. The samples for low frequency range are separated by substantially greater time periods, for example only every fourth digitized value need be saved in the low frequency buffer.

By way of example, the samples in the high frequency buffer are subjected to a one hundred and twenty-eight point FFT while samples in the low frequency buffer are subjected to a thirty-two point FFT. The frequency spectrum or spectrums generated by one or more FFTs are analyzed for resonating frequencies.

A resonating feedback frequency is detected in step 436*a*. If there is no resonating feedback frequency the program returns to step 434. Once a resonating feedback frequency has been detected, the program in step 436*b* interpolates this into the appropriate filter control signals. Then in step 437 the filter parameters are set whereupon the program returns to the step 434.

When a resonating frequency is detected, the microprocessor assigns a selected notch filter and operates digital-to-analog convertor 428 to generate a corresponding control voltage. The corresponding sample and hold circuit 429 is operated to receive the control voltage and apply this control voltage via a line 418*a* to the selected notch filter 413*a*–413*f* of FIG. 24. This control voltage determines the decibel level necessary to attenuate the resonating feedback signal to a level where it is no longer resonating. The counter-timer circuit 430 connected to the selected filter by lines 418*b* is set by the microprocessor to operate the notch filter at the detected resonating feedback frequency so as to filter the narrow frequency band containing the feedback frequency.

Figure 24:
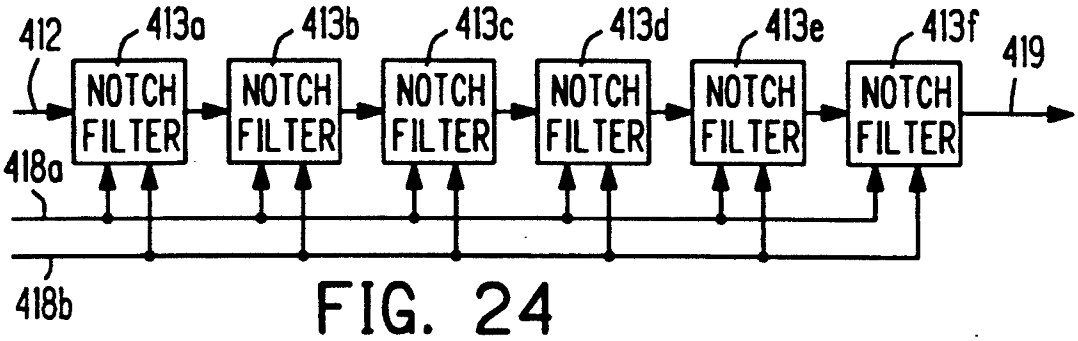
FIG. 24 is a detailed block diagram of a notch filter array of the circuit of FIG. 20.
Figure 25:
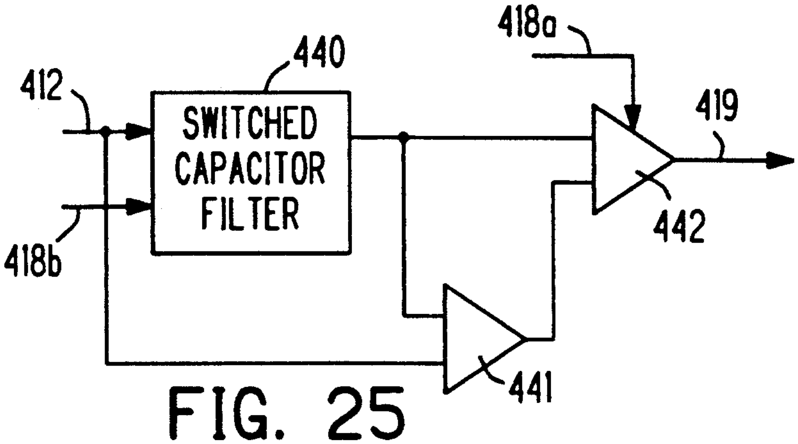
FIG. 25 is a detailed diagram of a notch filter of the array of FIG. 24.

Referring to FIG. 25, a typical notch filter circuit employs a conventional switched capacitance notch filter 440 which receives the analog signal on line 412, the depth control signal on line 418*a* and the frequency control signals on lines 418*b*. Amplifier 441 and voltage controlled amplifier 442 provide for the variable control of the filter depth. The input 412 is also applied to an input of the amplifier 441 along with the output of the filter unit 440 so as to generate a bandpass of the filtered band. The output of the amplifier 441 is applied to one input of the amplifier 442 which receives on its other input the output of the filter unit 440 so as to variably control the amplitude of the rejected frequency band in the output 419. The amplitude of the rejected frequency band is reduced or attenuated compared to the remaining unfiltered frequencies. As shown in FIG. 24, six frequency bands can be attenuated from the input signal as the signal passes from through the filters 413*a*–413*f* to the output 419.

Figure 26:
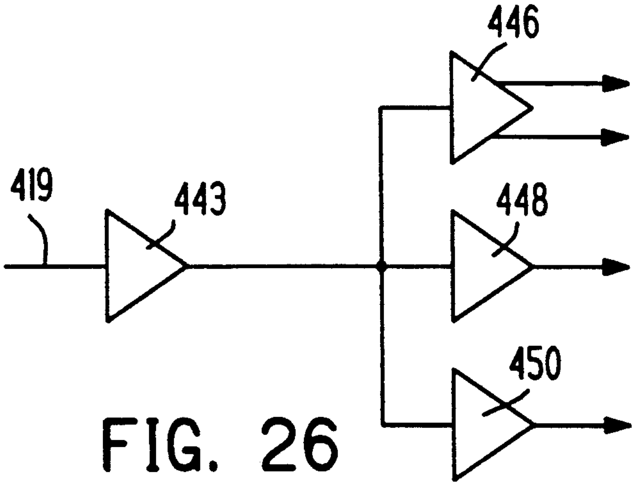
FIG. 26 is a detailed diagram of an output portion of the circuit of FIG. 20.

A typical output circuit is shown in FIG. 26 to include a buffer amplifier 443 receiving the filter output 419 and passing the output to amplifiers 446, 448 and 450 which in turn restore the original input signal configuration. The outputs can set the output voltages to the levels of the original input signals 410*a*–410*c*.

In operation of the circuit of FIGS. 20–25, the unit is installed between a microphone and amplifier in a sound amplification system. When the amplification system is activated, the microprocessor 417 automatically samples the incoming digitized signals, conducts a Fast Fourier Transform on a selected group of the digitized signals to produce a frequency spectrum, and analyzes this frequency spectrum to detect a resonating feedback frequency. The detection of a resonating feedback frequency causes the microprocessor to set a first of the notch filters 413*a* to eliminate the feedback. The program continues to detect any additional resonating feedback frequencies. Generally, several resident or natural feedback frequencies will be detected in a given room or area and the first three of the six independently programmable filters will be set to provide fixed notches eliminating the first three of the detected resonating feedback frequencies. Any additional feedback frequencies are assigned to the remaining filters. When the microprocessor finds that upon the detection of a new feedback frequency the number of feedback frequencies now exceed six, the program automatically selects one of the non-fixed filters to filter the newly detected feedback frequency and disables the filtering of the old feedback frequency by the selected filter.

While the above description particularly discloses the elimination of resonant feedback signals from an audio amplification system, the disclosed method and apparatus can be used to eliminate feedback in other types of electrical amplification systems where resonance can occur.

Since many modifications, variations and changes in detail can be made to the embodiments described above, it is intended that the foregoing description and the accompanying drawings be interpreted as being only illustrative, and that many other embodiments can be devised without departing from the scope and spirit of the invention as defined in the following claims.

What is claimed is:

1. An apparatus for eliminating acoustical feedback in a system which includes a microphone for converting audible acoustic signals into electrical signals, an amplifier for amplifying the electrical signals from the microphone, and a speaker for converting the amplified electrical signals into amplified audible acoustic signals and for broadcasting the amplified acoustic signals in the vicinity of the microphone, the apparatus comprising analog-to-digital convertor means for digitizing the electrical signals and for periodically producing a predetermined series of digital signals corresponding to a predetermined time segment of the electrical signals;

computer means including fast Fourier transform means for converting each series of digital signals into a frequency spectrum, means for examining successive frequency spectrums to determine the presence of an undesirable acoustic feedback, and means for generating frequency specific filter control signals in response to the determination of the presence of the undesirable acoustic feedback;

the frequency spectrum examining means including means for determining a maximum magnitude frequency, mean for determining whether a magnitude of the maximum magnitude frequency is greater than a magnitude of a selected harmonic of the maximum magnitude frequency by at least a predetermined factor to indicate a candidate resonant frequency, and means for determining the presence of a candidate resonant frequency in a plurality of a predetermined number of successive spectrums to indicate the candidate resonant frequency as the undesirable acoustic feedback; and filter means controlled by the filter control signals form the computer means for attenuating one or more narrow frequency bands in the electrical signal to eliminate the undesirable acoustic feedback.

2. An apparatus as claimed in claim 1 wherein the frequency spectrum examining means includes means for determining a plurality of largest magnitude frequencies, and means for determining whether a magnitude of each of the largest magnitude frequencies is greater than a magnitude of a selected harmonic of each respective largest magnitude frequency by at least a predetermined factor to indicate each largest magnitude frequency as a candidate resonant frequency.

3. An apparatus as claimed in claim 1 wherein the predetermined factor is equal to or greater than 20 decibels.

4. An apparatus as claimed in claim 1 wherein the predetermined factor is equal to or greater than 33 decibels.

5. An apparatus as claimed in claim 1 wherein the means for determining whether the magnitude of the maximum magnitude frequency is greater than the magnitude of a selected harmonic of the maximum magnitude frequency by at least a predetermined factor includes means for determining whether the magnitude of the maximum magnitude frequency is greater than a magnitude of a first and second higher harmonics and a first subharmonic of the maximum magnitude frequency by at least a predetermined factor to indicate a candidate resonant frequency.

6. An apparatus as claimed in claim 1 wherein the predetermined number is at least three.

7. An apparatus as claimed in claim 6 wherein the predetermined number is at least five.

8. An apparatus as claimed in claim 1 wherein the means for determining the presence of a candidate resonant frequency determines the presence of a candidate resonant frequency in at least three of five successive spectrums to indicate the candidate resonant frequency as a resonant frequency.

9. An apparatus as claimed in claim 1 wherein the filter means includes (a) second computer means which includes means for receiving both the digitized signals from the analog-to-digital convertor mean and the control signals from a first computer means, digital filter means for attenuating one or more narrow bands of frequencies in the digital signals; and (b) digital-to-analog convertor means for converting ht filter digital signals into filtered analog signals.

10. An apparatus as claimed in claim 1 wherein the fast Fourier transform is performed with a first resolution in a low frequency range from a minimum audio frequency to a middle audio frequency and is performed with a second resolution in a high frequency range form the middle audio frequency at a maximum audio frequency, said first resolution being in a range from 1 to 3 Hertz and said second resolution being in a range from 5 to 30 Hertz.

11. An apparatus as claimed in claim 10 wherein the fast Fourier transform for the low frequency range is performed with one-hal for less of the predetermined series of digital signals.

12. An apparatus as claimed in claim 10 wherein successive pluralities of the predetermined series of digital signals are averaged to generate a series of average digital signals upon which the fast Fourier transform for the low frequency range is performed.

13. An apparatus as claimed in claim 1 in which the computer means includes software means for identifying a first preselected number of resonant feedback frequencies which are indicative of natural acoustics in an area in which the apparatus is placed and for controlling the filter means to continuously attenuate said preselected resonant frequencies.

14. An apparatus as claimed in claim 1 wherein the computer means upon indicating a resonant feedback frequency generates control signals to increase the attenuation of the resonant frequency by a predetermined amount.

15. An apparatus as claimed in claim 1 wherein the computer means includes setup means which in turn includes means for generating a flat frequency spectrum, means for converting the flat frequency spectrum into a digitized time domain time segment, digital-to-analog convertor means for generating an analog signal from the digitized time segment, means for applying the analog signal to the speaker, means for receiving and analyzing the electrical signal from the microphone to identify any resonant feedback frequencies, and means responsive to the receiving and analyzing mean for setting up filters to attenuate any such resonant feedback frequencies.

16. An apparatus as claimed in claim 1 wherein the filter means includes a plurality of analog notch filters operating on the electrical signal.

17. An apparatus as claimed in claim 1 wherein the means for determining whether the magnitude of the maximum magnitude frequency is greater than the magnitude of as elected harmonic comprises means for determining whether the magnitude of the maximum frequency is greater than the magnitudes of a plurality of selected harmonics of the maximum magnitude frequency by at least a predetermined factor to indicate a candidate resonant frequency.

18. An apparatus as claimed in claim 17 wherein the frequency spectrum examining means includes means for determining a plurality of largest magnitude frequencies, and means for determining whether a magnitude of each of the large magnitude frequencies is greater than magnitudes of a plurality of selected harmonics of each respective largest magnitude frequency by at least a predetermined factor to indicate each largest magnitude frequency as a candidate resonant frequency.

19. An apparatus as claimed in claim 17 wherein the predetermined factor is equal to or greater than 20 decibels.

20. An apparatus as claimed in claim 17 wherein the predetermined factor is equal to or greater than 33 decibels.

21. An apparatus as claimed in claim 1 wherein the means for determining whether the magnitude of the maximum magnitude frequency is greater than the magnitude of a selected harmonic comprises means for determining whether the magnitude of the maximum frequency is greater than magnitudes of a selected harmonic and a selected subharmonic of the maximum magnitude frequency by at least a predetermined factor to indicate a candidate resonant frequency.

22. An apparatus as claimed in claim 21 wherein the frequency spectrum examining means includes means for determining a plurality of largest magnitude frequencies, and means for determining whether a magnitude of each of the largest magnitude frequencies is greater than magnitudes of a selected harmonic and a selected subharmonic of each respective largest magnitude frequency by at least a predetermined factor to indicate each largest magnitude frequency as a candidate resonant frequency.

23. An apparatus as claimed in claim 1 wherein the filter means attenuates one or more frequency bands having widths less than one-fourth of an octave.

24. An apparatus as claimed in claim 23 wherein the frequency band or bands being attenuated have widths equal to or less than one-tenth of an octave.

25. A method of eliminating acoustical feedback in a system which includes a microphone for converting audible acoustic signals into electrical signals, an amplifier for amplifying the electrical signals from the microphone, and a speaker for converting the amplified electrical signals into amplified audible acoustic signals and for broadcasting the amplified acoustic signals in the vicinity of the microphone, the method comprising periodically digitizing a time segment of a predetermined duration of the electrical signals to produce a plurality of series of digital signals;

converting by a fast Fourier transform algorithm in computer means each of the plurality of series of digital signals into a frequency spectrum;

examining the frequency spectrums by the computer means to determine the presence of an undesirable acoustic feedback;

the examining of the frequency spectrums including determining a maximum magnitude frequency, determining whether a magnitude of the maximum magnitude frequency is greater than a magnitude of a selected harmonic of the maximum magnitude frequency by at least a predetermined factor to indicate a candidate resonant frequency, and determining the presence of a candidate resonant frequency in a plurality of a predetermined number of successive spectrums to indicate the candidate resonant frequency as the undesirable acoustic feedback;

generating frequency specific filter control signals by the computer means in response to the determination of the presence of the undesirable acoustic feedback; and attenuating one or more narrow frequency bands in the electric signal by controlling filter means by the filter control signals from the computer means to eliminate the undesirable acoustic feedback.

26. A method as claimed in claim 25 wherein said attenuation of one or more narrow frequency bands in the electrical signal is performed by digitizing the electrical signals, passing the digitized electrical signals to second computer means, passing the control signals from a first computer means to the second computer means, attenuating one or more narrow bands of frequencies in the digital signals by digital filter means in the second computer means in accordance with the filter control signals, and converting the attenuated digital signals into filtered analog signals.

27. An apparatus for eliminating acoustical feedback in a system which includes a microphone for converting audible acoustic signals into electrical signals, an amplifier for amplifying the electrical signals from the microphone, and a speaker for converting the amplified electrical signals into amplified audible acoustic signals and for broadcasting the amplified acoustic signals in the vicinity of the microphone, the apparatus comprising analog-to-digital convertor means for digitizing the electrical signals from the microphone;

first and second microcomputers for receiving digitized electrical signals;

said first microcomputer including means for receiving the digitized signals from the analog-to-digital convertor means, means for examining the digitized electrical signals to determine the presence of an undesirable acoustic feedback, means for generating frequency specific filter control signals in response to the determination of the presence of the undesirable acoustic feedback, and means for transmitting the digitized signals along with the frequency specific control signals;

said second microcomputer including means for receiving the digitized signals along with the frequency specific filter control signals from the first microcomputer, and filter means controlled by the filter control signals for attenuating one or more narrow frequency bands in the digitized electrical signals to produce filtered digitized electrical signals from which the undesirable acoustic feedback is eliminated; and digital-to analog convertor means for converting the filtered digitized electrical signals into filtered analog signals for driving said amplified and said speaker.

28. An apparatus as claimed in claim 27 wherein the means for examining the digitized electrical signals includes means for determining the presence of a frequency component in the digitized electrical signals having a magnitude which exceeds by at least twenty decibels a magnitude of each of a plurality of selected harmonic frequency components in the digitized signals for a substantial duration.

29. An apparatus as claimed in claim 27 wherein the means for examining the digitized electrical signals includes means for determining the presence of a frequency component in the digitized electrical signals having a magnitude which exceeds by at least twenty decibels each of a selected harmonic frequency component and a selected subharmonic frequency component in the digitized signals for a substantial duration.

30. An apparatus for eliminating acoustical feedback in a system which includes a microphone for converting audible acoustic signals into electrical signals, an amplifier for amplifying the electrical signals from the microphone, and a speaker for converting the amplified electrical signals into amplified audible acoustic signals and for broadcasting the amplified acoustic signals in the vicinity of the microphone, the apparatus comprising means for sensing in the electrical signals from the microphone the presence of a frequency component having ga magnitude which exceeds by at least twenty decibels the magnitudes of each of a plurality of selected harmonic components in the electrical signals for a substantial duration to determine a resonating feedback frequency component; and filer means controlled by the sensing means for attenuating said resonating feedback frequency component in the electrical signals from the microphone to produce filtered electrical signals from which the resonating feedback frequency component is eliminated for driving said amplifier and said speaker.

31. An apparatus as claimed in claim 30 wherein the sensing means comprises analog-to-digital convertor means for digitizing the electrical signals to produce a plurality of series of digital signals corresponding to time segments of the electrical signals; and computer means including fast Fourier transform means for transforming each of the plurality of series of digital signals to produce a plurality of frequency spectrums, means for determining a plurality of a largest magnitude frequency components in each of the frequency spectrums and for indicating as a candidate resonant frequency each of the determined largest magnitude frequency components having a magnitude exceeding by at least twenty decibels magnitudes of a plurality of selected harmonics of the corresponding determined largest magnitude frequency component, and means responsive to a candidate resonant frequency being present in a predetermined number of the plurality of frequency spectrums for indicating such candidate resonant frequency as a resonating feedback frequency component.

32. An apparatus as claimed in claim 30 wherein the filter means comprise analog-to-digital convertor means for digitizing the electrical signals from the microphone, computer means for receiving the digitized electrical signals, and digital-to-analog convertor means for converting filtered digitized electrical signals from the computer means to analog electrical signals for driving said amplifier and said speaker, said computer means including a digital filter algorithm for attenuating a narrow bandwidth of frequencies including said resonating frequency component in the digitized electrical signals to produce the filtered digitized electrical signals.

33. An apparatus as claimed in claim 31 wherein the filter means comprises second computer means for receiving the digitized electrical signals, and digital-to-analog convertor means for converting filtered digitized electrical signals from the second computer means to analog electrical signals for driving said amplifier and said speaker, said second computer means including a digital filter algorithm for attenuating a narrow bandwidth of frequencies including said resonating frequency component in the digitized electrical signals to produce the filtered digitized electrical signals.

34. An apparatus as claimed in claim 30 wherein the filter means attenuates one or more frequency band having widths less than one-fourth of an octave.

35. An apparatus as claimed in claim 34 wherein the frequency band or bands being attenuated have widths equal to or less than one-tenth of an octave.

36. An apparatus as claimed in claim 30 wherein the sensing means must sense a magnitude of a frequency component exceeding by thirty-three or more decibels the magnitudes of the plurality of selected harmonics to determine a resonating feedback frequency component.

37. An apparatus for eliminating acoustical feedback in a system which includes a microphone for converting audible acoustic signals into electrical signals, an amplifier for amplifying the electrical signals from the microphone, and a speaker for converting the amplified electrical signals into amplified audible acoustic signals and for broadcasting the amplified acoustic signals in the vicinity of the microphone, the apparatus comprising analog-to-digital convertor mean for digitizing the electrical signals and for periodically producing a predetermined series of digital signals corresponding to a predetermined time segment of the electrical signals;

computer means including fast Fourier transform means for converting each series of digital signals into a frequency spectrum, means for examining successive frequency spectrums to determine the presence of an undesirable acoustic feedback, and means for generating frequency specific filter control signals in response to the determination of the presence of the undesirable acoustic feedback;

the frequency spectrum examining mean including means for determining a maximum magnitude frequency, means for determining whether a magnitude of the maximum magnitude frequency is greater than a magnitude of as elected subharmonic of the maximum magnitude frequency by at least a predetermined factor to indicate a candidate resonant frequency, and means for determining the presence of a candidate resonant frequency in a plurality of a predetermined number of successive spectrums to indicate the candidate resonant frequency as the undesirable acoustic feedback; and filter means controlled the filter control signals from the computer means for attenuating one or more narrow frequency bands in the electric signal to eliminate the undesirable acoustic feedback.

38. An apparatus as claimed in claim 37 wherein the frequency spectrum examining means includes mean for determining a plurality of largest magnitude frequencies, and means for determining whether a magnitude of each of the largest magnitude frequencies is greater than a magnitude of a selected subharmonic of each respective largest magnitude frequency by at least a predetermined factor to indicate each largest magnitude frequency as a candidate resonant frequency.

39. An apparatus as claimed in claim 37 wherein the predetermined factor is equal to or greater than 20 decibels.

40. An apparatus as claimed in claim 37 wherein the predetermined factor is equal to or greater than 33 decibels.

41. An apparatus for eliminating acoustical feedback in a system which includes a microphone for converting audible acoustic signals into electrical signals, an amplifier for amplifying the electrical signals from the microphone, and a speaker for converting the amplified electrical signals into amplified audible acoustic signals and for broadcasting the amplified acoustic signals in the vicinity of the microphone, the apparatus comprising means for sensing in the electrical signals from the microphone the presence of a frequency component having the magnitude which exceeds by at least twenty decibels magnitudes of each of a selected harmonic component and a selected subharmonic component in the electrical signals for a substantial duration to designate the frequency component as an undesirable acoustic feedback; and filter means controlled by the sensing means for attenuating said undesirable acoustic feedback in the electrical signals from the microphone to produce filtered electrical signals from which said undesirable acoustic feedback is eliminated for driving said amplifier and said speaker.

42. An apparatus as claimed in claim 41 wherein the sensing means comprises analog-to-digital convertor means for digitizing the electrical signals to produce a plurality of series of digital signals corresponding to time segments of the electrical signals; and computer means including fast Fourier transform means for transforming each of the plurality of series of digital signals to produce a plurality of frequency spectrums, means for determining a plurality of largest magnitude frequency components in each of the frequency spectrums and for indicating as a candidate resonant frequency each of the determined largest magnitude frequency components having a magnitude exceeding by at least twenty decibels magnitudes of a selected harmonic and a selected subharmonic of the corresponding determined largest magnitude frequency component, and means responsive to a candidate resonant frequency being presenting a predetermined number of the plurality of frequency spectrums for indicating such candidate resonant frequency as a resonating feedback frequency component.

43. An apparatus as claimed in claim 41 wherein the filter means comprises analog-to-digital convertor means for digitizing the electrical signals from the microphone, computer means for receiving the digitized electrical signals, and digital-to-analog convertor means for converting filtered digitized electrical signals from the computer means to analog electrical signals for driving said amplifiers and said speaker, said computer means including a digital filter algorithm for attenuating a narrow bandwidth of frequencies including said resonating frequency component in the digitized electrical signal to produce the filtered digitized electrical signals.

44. An apparatus as claimed in claim 40 wherein the filter means comprises second computer means for receiving the digitized electrical signals, and digital-to-analog convertor means for converting filtered digitized electrical signals from the second computer means to analog electrical signal for driving said amplifier and said speaker, said second computer means including a digital filter algorithm for attenuating a narrow bandwidth of frequencies including said resonating frequency component in the digitized electrical signals to produce the filtered digitized electrical signals.

45. An apparatus for eliminating acoustical feedback in a system which includes a microphone for converting audible acoustic signals into electrical signals, an amplifier for amplifying the electrical signals from the microphone, and a speaker for converting the amplified electrical signals into amplified audible acoustic signals and for broadcasting the amplified acoustic signals in the vicinity of the microphone, the apparatus comprising means for sensing the presence of an acoustical frequency component having a magnitude which exceeds by at least twenty decibels a magnitude of a selected harmonic of the acoustical component for a substantial duration to designate the acoustical frequency component as an undesirable acoustic feedback; and filter means controlled by the sensing means for attenuating a narrow bandwidth encompassing the designated undesirable acoustic feedback in the electrical signals from the microphone to produce filtered electrical signals from which the undesirable acoustic feedback is eliminated for driving said amplifier and said speaker.

46. An apparatus as claimed in claim 45 wherein the sensing means comprises analog-to-digital convertor means for digitizing electrical signals to produce a plurality of series of digital signals corresponding to time segments of the electrical signals; and computer means including fast Fourier transform means for transforming each of the plurality of series of digital signals to produce a plurality of frequency spectrums, means for determining a plurality of largest magnitude frequency components in each of the frequency spectrums and for indicating as a candidate resonant frequency each of the determined largest magnitude frequency components having a magnitude exceeding by at least twenty decibels magnitudes of a plurality of selected harmonics of the corresponding determined largest magnitude frequency component, and means responsive to a candidate resonant frequency being present in a predetermined number of the plurality of frequency spectrums for indicating such candidate resonant frequency as a resonating feedback frequency component.

47. An apparatus as claimed in claim 45 wherein the filter means comprises analog-to-digital convertor means for digitizing the electrical signals from the microphone, computer means for receiving the digitized electrical signals, and digital-to-analog convertor means for converting filtered digitized electrical signals from the computer means to analog electrical signals for driving said amplified and said speaker, said computer means including a digital filter algorithm for attenuating a narrow bandwidth of frequencies including said resonating frequency component in the digitized electrical signals to produce the filtered digitized electrical signals.

48. An apparatus as claimed in claim 46 wherein the filter means comprises second computer means for receiving the digitized electrical signals, and digital-to-analog convertor means for converting filtered digitized electrical signals from the second computer means to analog electrical signals for driving said amplifier and said speaker, said second computer means including a digital filer algorithm for attenuating a narrow bandwidth of frequencies including said resonating frequency component in the digitized electrical signals to produce the filtered digitized electrical signals.

49. An apparatus as claimed in claim 45 wherein the filter means attenuates one or more frequency bands having widths less than one-tenth of an octave.

50. An apparatus as claimed in claim 45 wherein the sensing means must sense a magnitude of a frequency component exceeding by thirty-three or more decibels the magnitude of a selected harmonic to determine a resonating feedback frequency component.

51. An apparatus as claimed in claim 45 wherein the sensing means senses the presence of a frequency component having a magnitude which exceeds by at least twenty decibels magnitudes of each of a plurality of selected harmonic components in the electrical signals for a substantial duration to determine a resonating feedback frequency component.

52. An apparatus as claimed in claim 45 wherein the selected harmonic is a 1.5 harmonic, a first harmonic, a second harmonic or a first subharmonic.

53. An apparatus as claimed in claim 46 wherein the plurality of selected harmonics include a 1.5 harmonic, a first harmonic, a second harmonic and a first subharmonic.

* * * * *